(12) United States Patent
Hiramatsu

(10) Patent No.: US 11,774,393 B2
(45) Date of Patent: Oct. 3, 2023

(54) SENSOR AND CAPACITOR DEVICE

(71) Applicant: KABUSHIKI KAISHA TOSHIBA, Tokyo (JP)

(72) Inventor: Naoki Hiramatsu, Yokohama Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 17/863,366

(22) Filed: Jul. 12, 2022

(65) Prior Publication Data

US 2023/0280299 A1 Sep. 7, 2023

(30) Foreign Application Priority Data

Mar. 2, 2022 (JP) ................................. 2022-031671

(51) Int. Cl.
*G01N 27/24* (2006.01)
*G01N 27/22* (2006.01)

(52) U.S. Cl.
CPC ............ *G01N 27/24* (2013.01); *G01N 27/226* (2013.01)

(58) Field of Classification Search
CPC .............................. G01N 27/24; G01N 27/226
See application file for complete search history.

(56) References Cited

U.S. PATENT DOCUMENTS

| 11,085,836 | B2* | 8/2021 | Okada | G01L 25/00 |
| 2016/0363553 | A1* | 12/2016 | Alexeenko | G01L 9/00 |
| 2019/0086377 | A1 | 3/2019 | Ikehashi et al. | |
| 2020/0011827 | A1* | 1/2020 | Zhou | G01N 27/226 |
| 2020/0080954 | A1* | 3/2020 | Yamazaki | G01N 27/128 |
| 2022/0018820 | A1* | 1/2022 | Hiramatsu | G01N 27/226 |

FOREIGN PATENT DOCUMENTS

JP 2019-56607 A 4/2019

\* cited by examiner

*Primary Examiner* — Alvaro E Fortich
(74) *Attorney, Agent, or Firm* — Finnegan, Henderson, Farabow, Garrett & Dunner, LLP

(57) ABSTRACT

According to one embodiment, a sensor includes a sensor element. The sensor element includes a first base body, a first fixed electrode fixed to the first base body, and a first structure body. The first structure body includes a first fixed portion fixed to the first base body, a first deformable portion supported by the first fixed portion, a first intermediate portion supported by the first deformable portion, and a first movable portion supported by the first intermediate portion. The first deformable portion includes a first deformed facing surface facing the first base body, and a first deformable surface. The first intermediate portion includes a first intermediate facing surface facing the first base body, and a first intermediate surface. The first deformable surface is possible to be deformed depending on a gas included in a space around the first structure body.

20 Claims, 17 Drawing Sheets

SENSOR AND CAPACITOR DEVICE

CROSS-REFERENCE TO RELATED APPLICATIONS

This application is based upon and claims the benefit of priority from Japanese Patent Application No. 2022-031671, filed on Mar. 2, 2022; the entire contents of which are incorporated herein by reference.

FIELD

Embodiments described herein relate generally to a sensor and a capacitor device.

BACKGROUND

For example, it is desired for a sensor to improve characteristics.

DETAILED DESCRIPTION

Figure 1A:
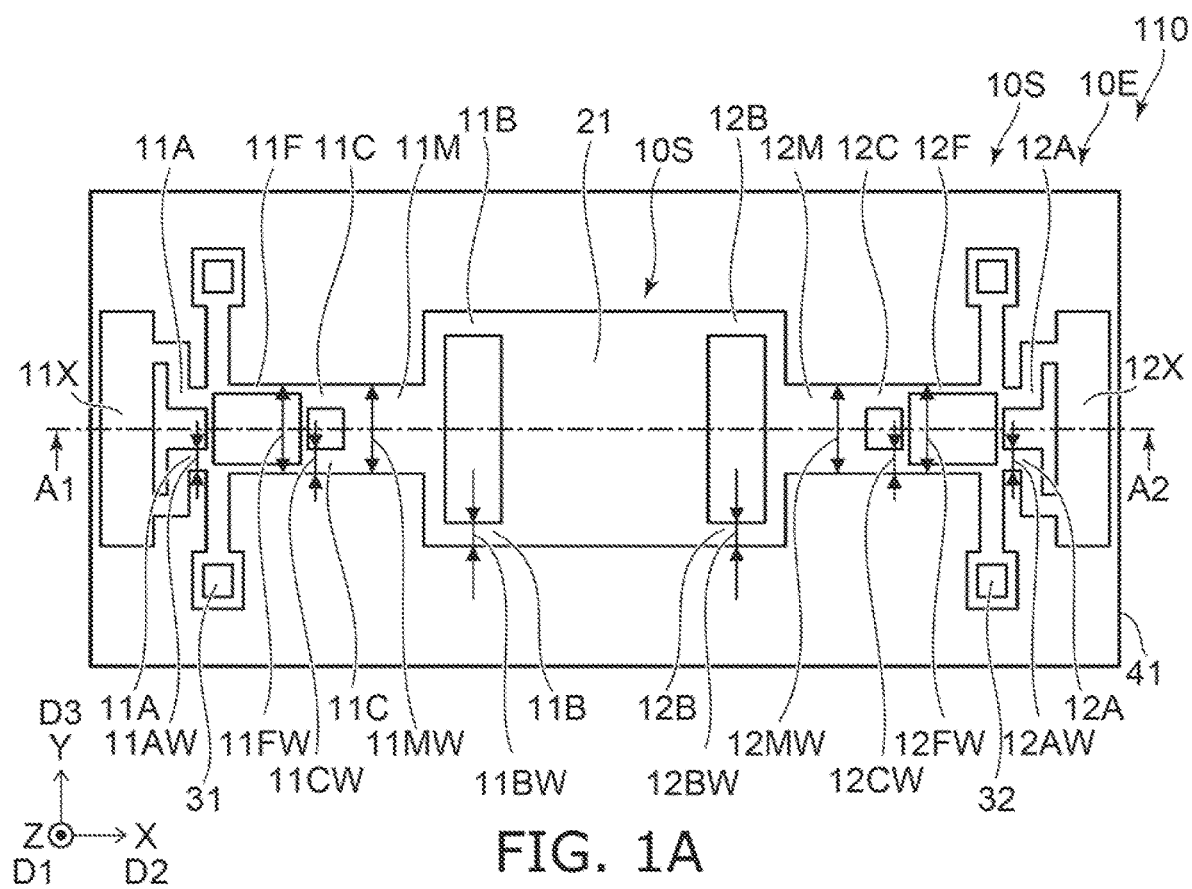
FIGS. 1A and 1B are schematic views illustrating a sensor according to a first embodiment.

According to one embodiment, a sensor includes a sensor element. The sensor element includes a first base body, a first fixed electrode fixed to the first base body, and a first structure body. The first structure body includes a first fixed portion fixed to the first base body, a first deformable portion supported by the first fixed portion, a first intermediate portion supported by the first deformable portion, and a first movable portion supported by the first intermediate portion. The first movable portion includes a first movable electrode facing the first fixed electrode. A first gap is provided between the first base body and the first deformable portion, and between the first base body and the first intermediate portion. A third gap is provided between the first fixed electrode and the first movable electrode. The first deformable portion includes a first deformed facing surface facing the first base body, and a first deformable surface. The first deformed facing surface is between the first base body and the first deformable surface in a first direction from the first base body to the first movable portion. The first intermediate portion includes a first intermediate facing surface facing the first base body, and a first intermediate surface. The first intermediate facing surface is between the first base body and the first intermediate surface in the first direction. The first deformable surface is possible to be deformed depending on a gas included in a space around the first structure body. With a rise of a temperature, the first deformable surface deforms into one of a concave shape and a convex shape, and the first intermediate surface deforms into an other of the concave shape and the convex shape.

According to one embodiment, a capacitor device includes a first base body, a first fixed electrode fixed to the first base body, a first structure body, and a controller. The first structure body includes a first fixed portion fixed to the first base body, a first deformable portion supported by the first fixed portion, a first intermediate portion supported by the first deformable portion, and a first movable portion supported by the first deformable portion. The first deformable portion includes a first resistance layer. The first movable portion includes a first movable electrode facing the first fixed electrode. A first gap is provided between the first base body and the first deformable portion and between the first base body and the first intermediate portion. A third gap is provided between the first fixed electrode and the first movable electrode. The first deformable portion includes a first deformed facing surface facing the first base body, and a first deformable surface. The first deformed facing surface is between the first base body and the first deformable surface in a first direction from the first base body to the first movable portion. The first intermediate portion includes a first intermediate facing surface facing the first base body, and a first intermediate surface. The first intermediate facing surface is between the first base body and the first intermediate surface in the first direction. With a rise of a temperature, the first deformable surface is deformed into one of a concave shape or a convex shape, and the first intermediate surface is deformed into an other of the concave shape or the convex shape. The controller is configured to change a first capacitance between the first fixed electrode and the first movable electrode by supplying a current to the first resistance layer.

Various embodiments are described below with reference to the accompanying drawings.

The drawings are schematic and conceptual; and the relationships between the thickness and width of portions, the proportions of sizes among portions, etc., are not necessarily the same as the actual values. The dimensions and proportions may be illustrated differently among drawings, even for identical portions.

In the specification and drawings, components similar to those described previously or illustrated in an antecedent drawing are marked with like reference numerals, and a detailed description is omitted as appropriate.

First Embodiment

Figure 1B:
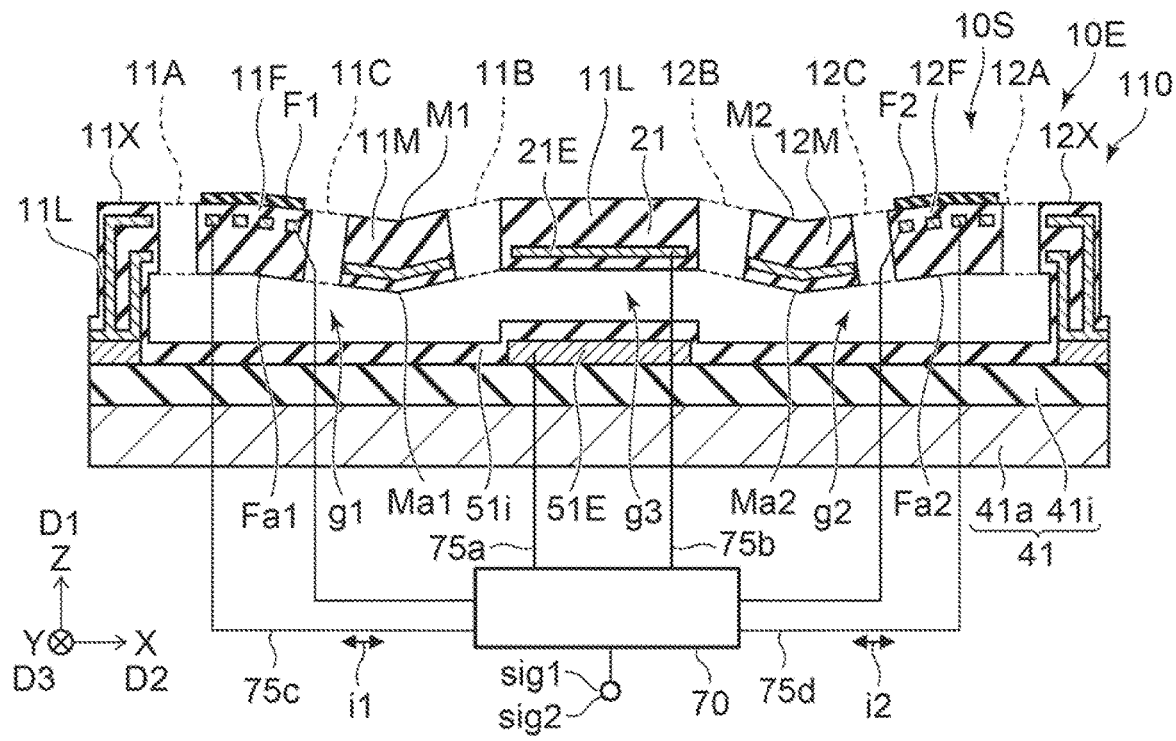

FIGS. 1A and 1B are schematic views illustrating a sensor according to the first embodiment. FIG. 1A is a plan view. FIG. 1B is a cross-sectional view taken along the line A1-A2 of FIG. 1A.

As shown in FIGS. 1A and 1B, a sensor 110 according to the embodiment includes a sensor element 10E. The sensor element 10E includes a first base body 41, a first fixed electrode 51E, and a first structure body 10S. The first fixed electrode 51E is fixed to the first base body 41.

As shown in FIG. 1B, in this example, the first base body 41 includes a substrate 41a and an insulating layer 41i. The substrate 41a may include, for example, a semiconductor substrate (for example, a silicon substrate). The insulating layer 41i is provided between the substrate 41a and the first fixed electrode 51E. In this example, an insulating layer 51i is provided on the first fixed electrode 51E.

The first structure body 10S includes a first fixed portion 11X, a first deformable portion 11F, a first intermediate portion 11M, and a first movable portion 21. The first fixed portion 11X is fixed to the first base body 41. The first deformable portion 11F is supported by the first fixed portion 11X. The first intermediate portion 11M is supported by the first deformable portion 11F. The first movable portion 21 is supported by the first intermediate portion 11M. The first movable portion 21 includes a first movable electrode 21E. The first movable electrode 21E faces the first fixed electrode 51E.

A first gap g1 is provided between the first base body 41 and the first deformable portion 11F, and between the first base body 41 and the first intermediate portion 11M. A gap (third gap g3) is provided between the first fixed electrode 51E and the first movable electrode 21E.

In this example, the first structure body 10S includes a first connection portion 11C, a first movable connection portion 11B, and a first fixed connection portion 11A. The first connection portion 11C connects the first deformable portion 11F and the first intermediate portion 11M. The first movable connection portion 11B connects the first intermediate portion 11M and the first movable portion 21. The first fixed connection portion 11A connects the first fixed portion 11X and the first deformable portion 11F.

The first movable portion 21 may include an insulating member 11L. The insulating member 11L is provided around the first movable electrode 21E, for example.

For example, the first fixed electrode 51E is provided on the first base body 41. The first movable portion 21 is provided above the first fixed electrode 51E.

As shown in FIG. 1B, the first deformable portion 11F includes a first deformed facing surface Fa1 and a first deformable surface F1. The first deformed facing surface Fa1 faces the first base body 41. The first deformed facing surface Fa1 is between the first base body 41 and the first deformable surface F1 in a first direction D1. The first direction D1 is a direction from the first base body 41 to the first movable portion 21. The first deformable surface F1 is a surface opposite to the first deformed facing surface Fa1. The first deformed facing surface Fa1 is, for example, a lower surface. The first deformable surface F1 is, for example, an upper surface.

The first intermediate portion 11M includes a first intermediate facing surface Ma1 and a first intermediate surface M1. The first intermediate facing surface Ma1 faces the first base body 41. The first intermediate facing surface Ma1 is between the first base body 41 and the first intermediate surface M1 in the first direction D1. The first intermediate facing surface Ma1 is, for example, a lower surface. The first intermediate surface M1 is, for example, an upper surface.

The first direction D1 is defined as a Z-axis direction. One direction perpendicular to the Z-axis direction is defined as an X-axis direction. A direction perpendicular to the Z-axis direction and the X-axis direction is defined as a Y-axis direction. The first direction D1 is, for example, a height direction.

The first deformable surface F1 can be deformed according to a gas included in a space around the first structure body 10S. For example, the gas includes a substance to be detected (for example, hydrogen). For example, a shape of the first deformable portion 11F changes according to a concentration of the substance to be detected.

For example, the first deformable portion 11F includes a first detection layer 11S. The first detection layer 11S adsorbs (or absorbs) the substance to be detected. With adsorption (or absorption), for example, the first detection layer 11S is deformed (for example, expanded). Along with this, the first deformable portion 11F is deformed, and the first deformable surface F1 is curved. On the other hand, the first intermediate portion 11M does not deform even if the concentration of the detection target changes.

On the other hand, the first deformable portion 11F and the first intermediate portion 11M are deformed in response to a change in temperature (for example, the temperature of the first structure body 10S). The directions of these deformations are different between the first deformable portion 11F and the first intermediate portion 11M. For example, as the temperature rises, the first deformable surface F1 and the first intermediate surface M1 are deformed in opposite directions to each other. For example, as the temperature rises, the first deformable surface F1 is deformed into one of a concave shape or a convex shape. The first intermediate surface M1 is deformed into the other of the concave shape and the convex shape.

FIG. 1B illustrates a high temperature state. In this example, in the high temperature state, the first deformable surface F1 is deformed in the concave shape, and the first intermediate surface M1 is deformed in the convex shape. As will be described later, in the high temperature state, the first deformable surface F1 may be deformed in the convex shape, and the first intermediate surface M1 may be deformed in the concave shape. As a result, more stable characteristics can be obtained.

Figure 2A:
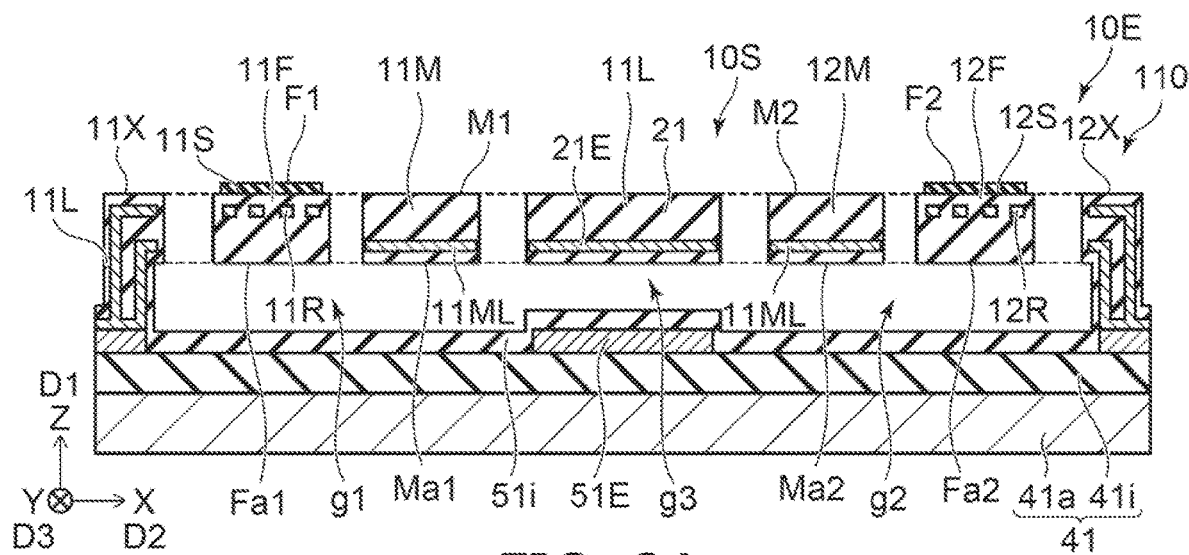
FIGS. 2A and 2B are schematic cross-sectional views illustrating the sensor according to the first embodiment.
Figure 2B:
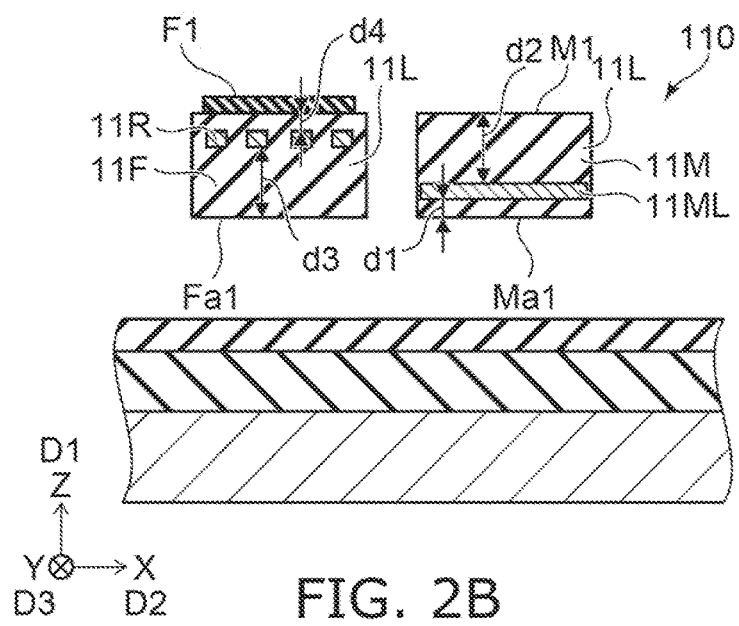

FIGS. 2A and 2B are schematic cross-sectional views illustrating the sensor according to the first embodiment.

FIG. 2A illustrates a low temperature state. The temperature in the low temperature state illustrated in FIG. 2A is lower than the temperature in the high temperature state illustrated in FIG. 1B. The temperature in the low temperature state is, for example, about 25° C. (not lower than 20° C. and not higher than 30° C.). The temperature in the high temperature state is, for example, not lower than 50° C. The temperature in the high temperature state may be, for example, not higher than 70° C.

As shown in FIG. 2A, the first deformable surface F1 of the first deformable portion 11F is substantially flat in the low temperature state. In the low temperature state, the first intermediate surface M1 of the first intermediate portion 11M is substantially flat.

On the other hand, in the high temperature state illustrated in FIG. 1B, the first deformable surface F1 of the first deformable portion 11F and the first intermediate surface M1 of the first intermediate portion 11M are curved. The direction of the curve is opposite to each other between the first deformable surface F1 and the first intermediate surface M1.

Such a structure is obtained, for example, by making the structure of the first deformable portion 11F asymmetric in the vertical direction and making the structure of the first intermediate portion 11M asymmetric in the vertical direction. For example, thermal expansion with a rise of a temperature deforms the asymmetric structure. This provides the curve in the opposite direction. An example of the asymmetric structure will be described later.

In the following, an example of deformation will be described.

Figure 3A:
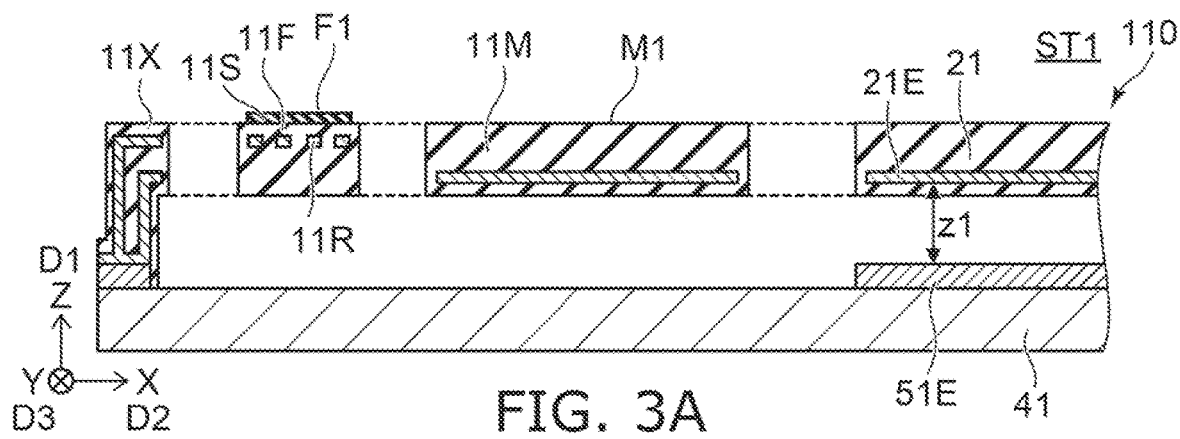
FIGS. 3A to 3C are schematic cross-sectional views illustrating the operation of the sensor according to the first embodiment.
Figure 3B:
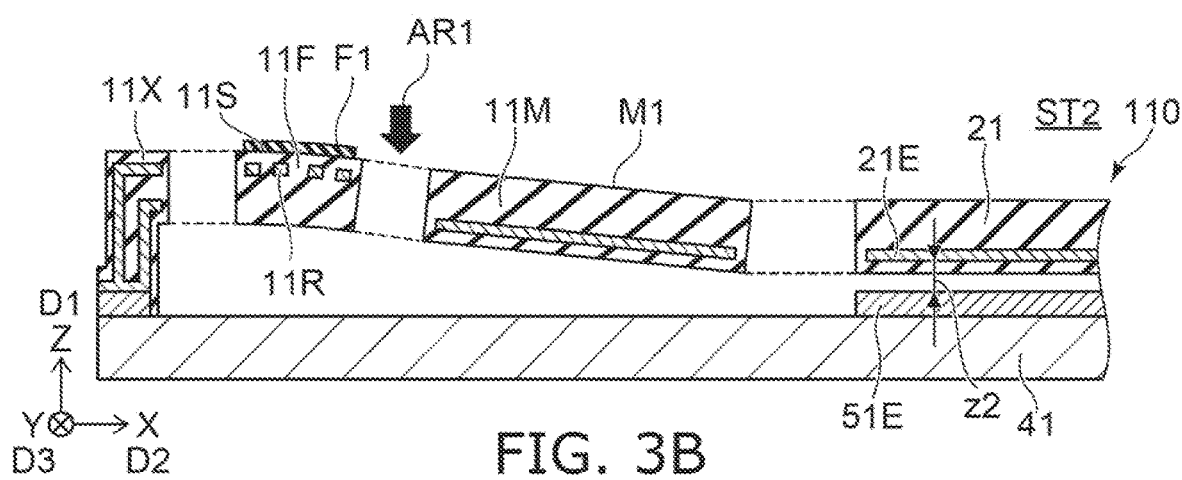
Figure 3C:
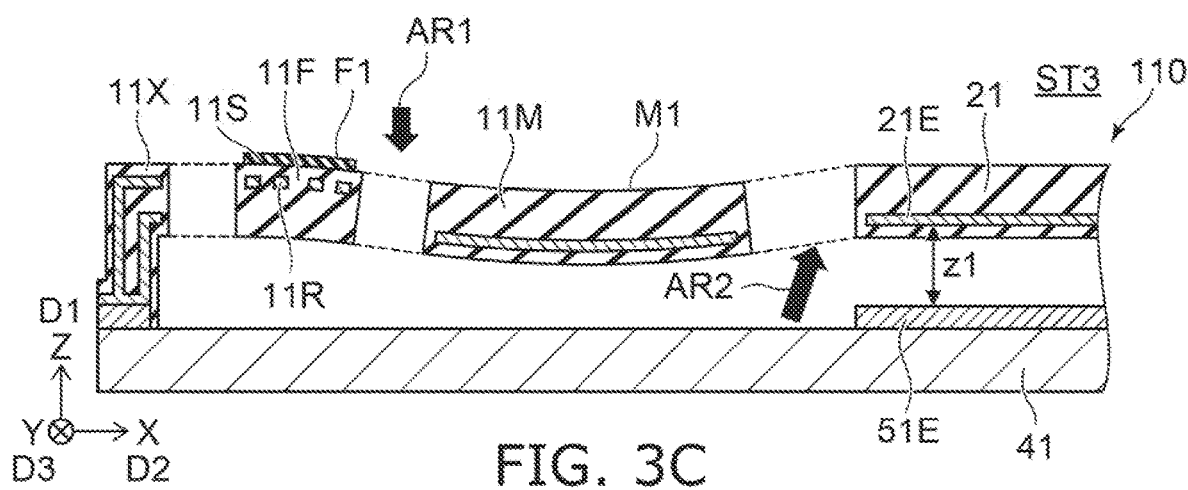

FIGS. 3A to 3C are schematic cross-sectional views illustrating the operation of the sensor according to the first embodiment.

A first state ST1 shown in FIG. 3A is the low temperature state, and in the first state ST1, the gas does not include the substance to be detected. In the first state ST1, the first deformable surface F1 and the first intermediate surface M1 are substantially flat. At this time, a distance between the first fixed electrode 51E and the first movable electrode 21E is a distance z1.

A second state ST2 shown in FIG. 3B is the low temperature state, and in the second state ST2, the gas includes the substance to be detected. In this case, the first deformable portion 11F is deformed according to the substance to be detected. When a concentration of the substance to be detected is high, the first deformable surface F1 is deformed convexly. An end of the first deformable surface F1 on a side of the first intermediate portion 11M is displaced in a direction of the arrow AR1 (for example, downward). As a result, a position of the first movable portion 21 in the second state ST2 in the height direction changes from a position of the first movable portion 21 in the first state ST1 in the height direction. In the second state ST2, a distance between the first fixed electrode 51E and the first movable electrode 21E is a distance z2. The distance z2 is shorter than the distance z1. This difference in distance is detected as a change in capacitance between the first fixed electrode 51E and the first movable electrode 21E.

A third state ST3 shown in FIG. 3C is the high temperature state, and in the third state ST3, the gas does not include the substance to be detected. In the third state ST3, for example, the first deformable surface F1 is deformed convexly due to the deformation caused by the thermal expansion. An end of the first deformable surface F1 on a side of the first intermediate portion 11M is displaced in the direction of the arrow AR1 (for example, downward). On the other hand, with the deformation caused by thermal expansion, for example, the first intermediate surface M1 is deformed in the concave shape. An end of the first intermediate surface M1 on a side of the first movable portion 21 is displaced in a direction of the arrow AR2 (for example, upward). As a result, a position of the first movable portion 21 in the third state ST3 in the height direction does not substantially change from the position of the first movable portion 21 in the first state ST1 in the height direction. For example, a distance between the first fixed electrode 51E and the first movable electrode 21E in the third state ST3 is the distance z1.

As described above, in the sensor 110 according to the embodiment, the change in the distance between the first fixed electrode 51E and the first movable electrode 21E due to the change in temperature can be suppressed. In the embodiment, the influence of temperature can be suppressed and the substance to be detected included in the gas can be detected with high accuracy.

Figure 4A:
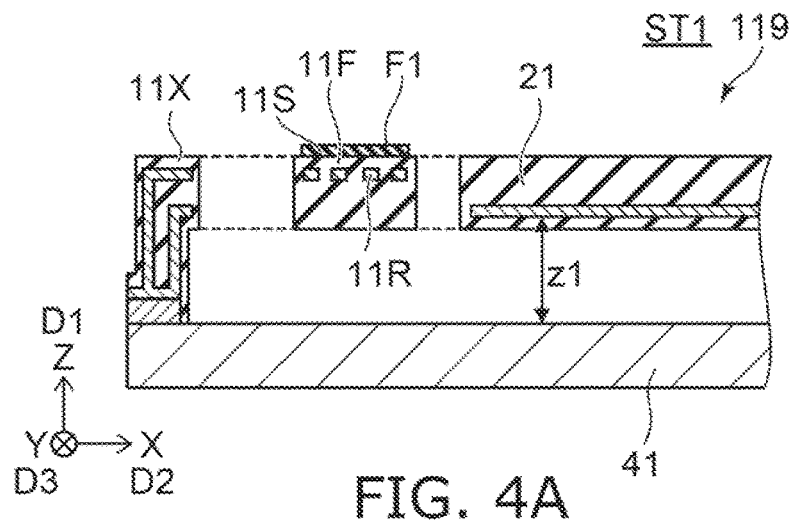
FIGS. 4A to 4C are schematic cross-sectional views illustrating the operation of a sensor according to a reference example.
Figure 4B:
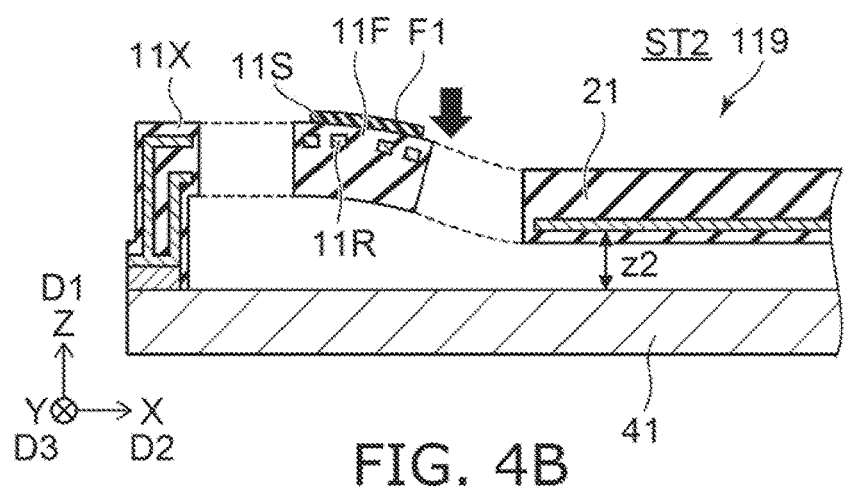
Figure 4C:
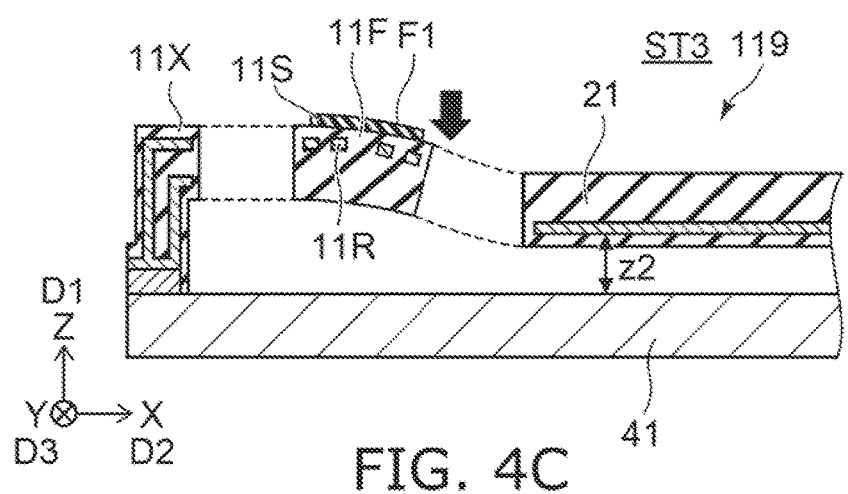

FIGS. 4A to 4C are schematic cross-sectional views illustrating the operation of a sensor according to a reference example.

These figures illustrate the operation of a sensor 119 of the reference example. The sensor 119 is not provided with the first intermediate portion 11M that deforms in the opposite direction to the first deformable portion 11F.

In the first state ST1 shown in FIG. 4A, the first deformable surface F1 and the first intermediate surface M1 are substantially flat. At this time, the distance between the first fixed electrode 51E and the first movable electrode 21E is the distance z1.

In the second state ST2 shown in FIG. 4B, the first deformable portion 11F is deformed in a convex shape according to the substance to be detected. The distance between the first fixed electrode 51E and the first movable electrode 21E in the second state ST2 is the distance z2. The distance z2 is shorter than the distance z1. This difference in distance is detected as a change in capacitance between the first fixed electrode 51E and the first movable electrode 21E.

In the third state ST3 shown in FIG. 4C, for example, the first deformable surface F1 is deformed convexly with the deformation caused by the thermal expansion. As a result, a position of the first movable portion 21 in the third state ST3 in the height direction changes from the position of the first movable portion 21 in the first state ST1 in the height direction. For example, the distance between the first fixed electrode 51E and the first movable electrode 21E in the third state ST3 is the distance z2.

As described above, in the sensor 119 of the reference example, the first intermediate portion 11M that deforms in the opposite direction to the first deformable portion 11F is not provided. In such a sensor 119, the distance between the first fixed electrode 51E and the first movable electrode 21E is affected by the temperature in addition to the concentration of the substance to be detected. Therefore, there is a limit to the improvement of accuracy in the detection of the substance to be detected.

On the other hand, in the embodiment, the influence of temperature can be suppressed. According to the embodiment, it is possible to provide a sensor whose characteristics can be improved.

As shown in FIGS. 2A and 2B, the first deformable portion 11F includes a first resistance layer 11R and the first detection layer 11S. The first detection layer 11S can be deformed depending on the gas. The first detection layer 11S is deformed, for example, depending on the concentration of the substance to be detected contained in the gas. At least a part of the first detection layer 11S may overlap the first resistance layer 11R in the first direction D1. As shown in FIG. 2B, the insulating member 11L may be provided around the first resistance layer 11R. For example, the first detection layer 11S may be provided on the surface of the insulating member 11L. The first resistance layer 11R is, for example, a heater.

The insulating member 11L may include, for example, at least one selected from the group consisting of oxygen and nitrogen, and silicon.

As shown in FIG. 2B, the first intermediate portion 11M may include a first intermediate conductive layer 11ML. The insulating member 11L may be provided around the first intermediate conductive layer 11ML. A distance along the first direction D1 between the first intermediate conductive layer 11ML and the first intermediate facing surface Ma1 is defined as a first distance d1. A distance along the first direction D1 between the first intermediate conductive layer 11ML and the first intermediate surface M1 is defined as a second distance d2. In the example shown in FIG. 2B, the first distance d1 is shorter than the second distance d2.

On the other hand, a distance along the first direction D1 between the first resistance layer 11R and the first deformed facing surface Fa1 is defined as a third distance d3. A distance along the first direction D1 between the first resistance layer 11R and the first deformable surface F1 is defined as a fourth distance d4. In the example shown in FIG. 2B, the third distance d3 is longer than the fourth distance d4.

In this way, a stacked structure of the layers is reversed between the first intermediate portion 11M and the first deformable portion 11F. As a result, the deformation in the opposite direction is obtained with respect to the change in temperature.

As will be described later, in the embodiment, the first distance d1 may be longer than the second distance d2, and the third distance d3 may be shorter than the fourth distance d4.

As shown in FIG. 1A, a first connection direction (in this example, the second direction D2 and the X-axis direction) from the first deformable portion 11F to the first intermediate portion 11M crosses the first direction D1. A width 11CW along a first connection crossing direction of at least a part of the first connection portion 11C is narrower than a width 11MW along the first connection crossing direction of the first intermediate portion 11M. The first connection crossing direction crosses a plane including the first direction D1 and the first connection direction. In this example, the first connection crossing direction is a third direction D3, for example, the Y-axis direction.

As shown in FIG. 1A, a first movable connection direction (in this example, the second direction D2 and the X-axis direction) from the first intermediate portion 11M to the first movable portion 21 crosses the first direction D1. A width 11BW along a first movable connection crossing direction of at least a part of the first movable connection portion 11B is narrower than a width 11MW along the first movable connection crossing direction of the first intermediate portion 11M. The first movable connection crossing direction crosses a plane including the first direction D1 and the first movable connection direction. In this example, the first movable connection crossing direction is the third direction D3, for example, the Y-axis direction.

As shown in FIG. 1A, a first fixed connection direction (in this example, the second direction D2 and the X-axis direction) from the first fixed portion 11X to the first deformable portion 11F crosses the first direction D1. A width 11AW along a first fixed connection crossing direction of at least a part of the first fixed connection portion 11A is narrower than a width 11FW along the first fixed connection crossing direction of the first deformable portion 11F. The first fixed connection crossing direction crosses a plane including the first direction D1 and the first fixed connection direction. In this example, the first fixed connection crossing direction is the third direction D3, for example, the Y-axis direction.

As shown in FIGS. 1A and 1B, the first structure body 10S may include a second fixed portion 12X fixed to the first base body 41 and a second deformable portion 12F supported by the second fixed portion 12X, and a second intermediate portion 12M supported by the second deformable portion 12F. The first movable portion 21 is supported by the first intermediate portion 11M and the second intermediate portion 12M. A second gap g2 is provided between the first base body 41 and the second deformable portion 12F, and between the first base body 41 and the second intermediate portion 12M.

The second deformable portion 12F includes a second deformed facing surface Fa2 facing the first base body 41 and a second deformable surface F2. The second deformed facing surface Fa2 is between the first base body 41 and the second deformable surface F2 in the first direction D1. The second intermediate portion 12M includes a second intermediate facing surface Ma2 facing the first base body 41 and a second intermediate surface M2. The second intermediate facing surface Ma2 is between the first base body 41 and the second intermediate surface M2 in the first direction D1.

The second deformable surface F2 can be deformed according to the gas included in the space. For example, as the temperature rises, the second deformable surface F2 is deformed to one of the concave shape or the convex shape, and the second intermediate surface M2 is deformed into the other of the concave shape or the convex shape.

The first movable portion 21 is between the first intermediate portion 11M and the second intermediate portion 12M. By providing the second fixed portion 12X, the second deformable portion 12F, and the second intermediate portion 12M in the first structure body 10S, the distance between the first fixed electrode 51E and the first movable electrode 21E becomes more stable.

In this example, the first structure body 10S includes a second connection portion 12C, a second movable connection portion 12B, and a second fixed connection portion 12A. The second connection portion 12C connects the second deformable portion 12F and the second intermediate portion 12M. The second movable connection portion 12B connects the second intermediate portion 12M and the first movable portion 21. The second fixed connection portion 12A connects the second fixed portion 12X and the second deformable portion 12F.

As shown in FIG. 1A, the first connection direction from the second deformable portion 12F to the second intermediate portion 12M (in this example, along the second direction D2 and along the X-axis direction) crosses the first direction D1. A width 12CW along a second connection crossing direction of at least a part of the second connection portion 12C is narrower than a width 12MW along the second connection crossing direction of the second intermediate portion 12M. The second connection crossing direction crosses a plane including the first direction D1 and the second connection direction. In this example, the second connection crossing direction is the third direction D3, for example, the Y-axis direction.

As shown in FIG. 1A, the first movable connection direction (in this example, along the second direction D2 and along the X-axis direction) from the second intermediate portion 12M to the first movable portion 21 crosses the first direction D1. A width 12BW along a second movable connection crossing direction of at least a part of the second movable connection portion 12B is narrower than a width 12MW along the second movable connection crossing direction of the second intermediate portion 12M. The second movable connection crossing direction crosses a plane including the first direction D1 and the second movable connection direction. In this example, the second movable connection crossing direction is along the third direction D3, for example, along the Y-axis direction.

As shown in FIG. 1A, a second fixed connection direction (in this example, along the second direction D2 and along the X-axis direction) from the second fixed portion 12X to the second deformable portion 12F crosses the first direction D1. A width 12AW along the second fixed connection crossing direction of at least a part of the second fixed connection portion 12A is narrower than a width 12FW along a second fixed connection crossing direction of the second deformable portion 12F. The first fixed connection crossing direction crosses a plane including the first direction D1 and the second fixed connection direction. In this example, the second fixed connection crossing direction is the third direction D3, for example, the Y-axis direction.

In this example, there is a second deformable portion 12F between the second fixed portion 12X and the first movable portion 21. There is the second intermediate portion 12M between the second deformable portion 12F and the first movable portion 21.

As shown in FIG. 2A, for example, the second deformable portion 12F includes a second resistance layer 12R and a second detection layer 12S. The second detection layer 12S can be deformed depending on the gas. The second detection layer 12S is deformed, for example, depending on the concentration of the substance to be detected contained in the gas. At least a part of the second detection layer 12S may overlap the second resistance layer 12R in the first direction D1. As shown in FIG. 2A, the insulating member 11L may be provided around the second resistance layer 12R. For example, the second detection layer 12S may be provided on the surface of the insulating member 11L.

In the sensor 110, the conductive layer electrically connected to the first movable electrode 21E may pass through the first fixed portion 11X and the second fixed portion 12X. For example, the conductive layer electrically connected to the first resistance layer 11R may pass through the first fixed portion 11X and the second fixed portion 12X. For example, the conductive layer electrically connected to the second resistance layer 12R may pass through the first fixed portion 11X and the second fixed portion 12X.

As shown in FIG. 1A, in this example, the first deformable portion 11F is supported by the tension provided by an anchor spring 31. The second deformable portion 12F is supported by the tension provided by an anchor spring 32. As a result, a stable support state can be obtained while suppressing heat conduction.

Figure 5A:
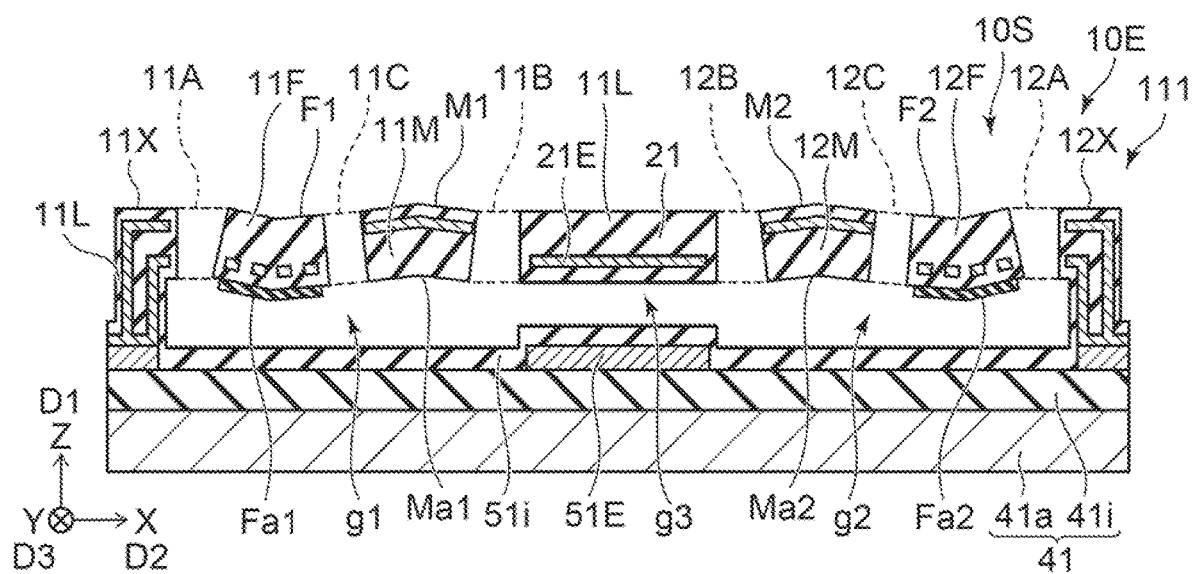
FIGS. 5A and 5B are schematic cross-sectional views illustrating a sensor according to the first embodiment.
Figure 5B:
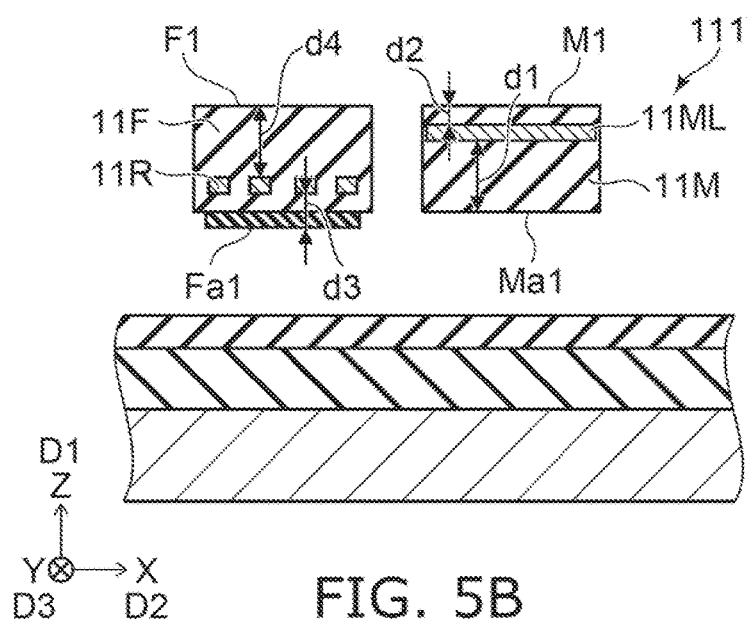

FIGS. 5A and 5B are schematic cross-sectional views illustrating a sensor according to the first embodiment.

As shown in FIG. 5A, in the sensor 111 according to the embodiment, the first deformable surface F1 is deformed into the concave shape and the first intermediate surface M1 is changed into the concave shape as the temperature rises. The influence of temperature can also be suppressed in the sensor 111.

As shown in FIG. 5B, the first distance d1 is longer than the second distance d2, and the third distance d3 is shorter than the fourth distance d4. Such a configuration causes deformation in the sensor 111. The configuration of the sensor 111 other than the above may be the same as the configuration of the sensor 110.

Figure 6:
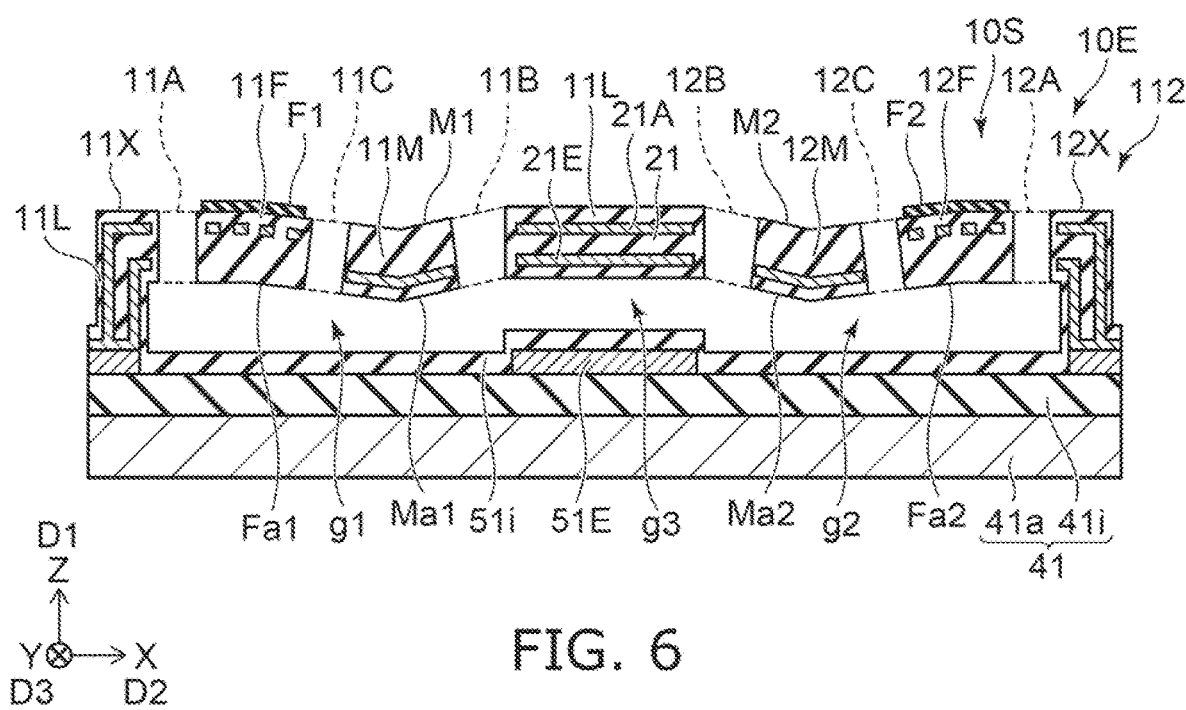
FIG. 6 is a schematic cross-sectional view illustrating a sensor according to the first embodiment.

FIG. 6 is a schematic cross-sectional view illustrating a sensor according to the first embodiment.

As shown in FIG. 6, in a sensor 112 according to the embodiment, the first movable portion 21 includes a conductive layer 21A in addition to the first movable electrode 21E. The conductive layer 21A is stacked with the first movable electrode 21E. The conductive layer 21A is, for example, the same layer as the first resistance layer 11R. The configuration of the sensor 112 other than the above may be the same as the configuration of the sensor 110.

Figure 7A:
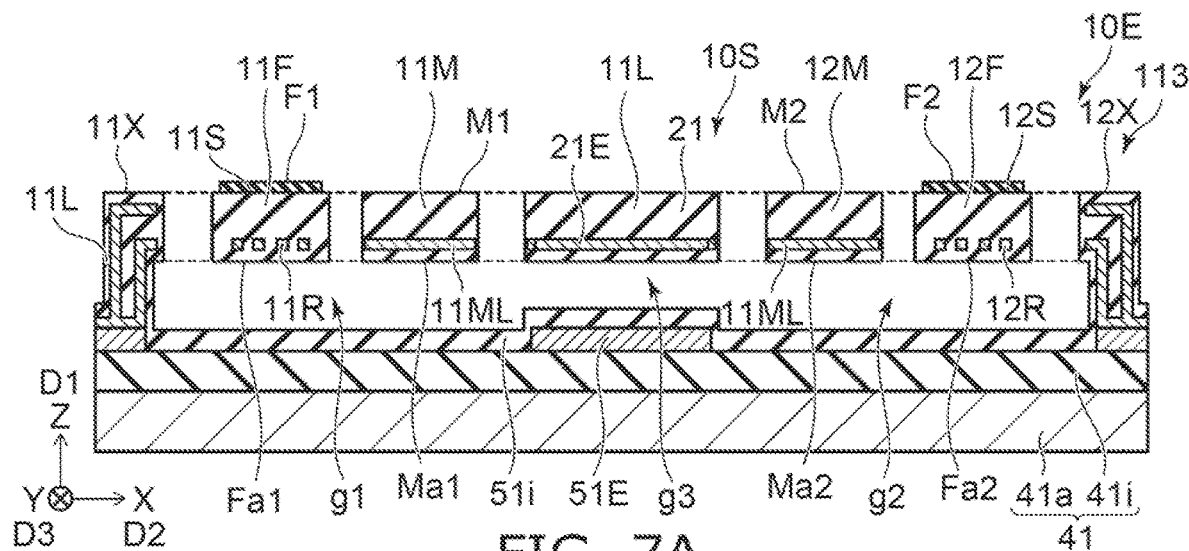
FIGS. 7A to 7C are schematic cross-sectional views illustrating the operation of a sensor according to the first embodiment.
Figure 7B:
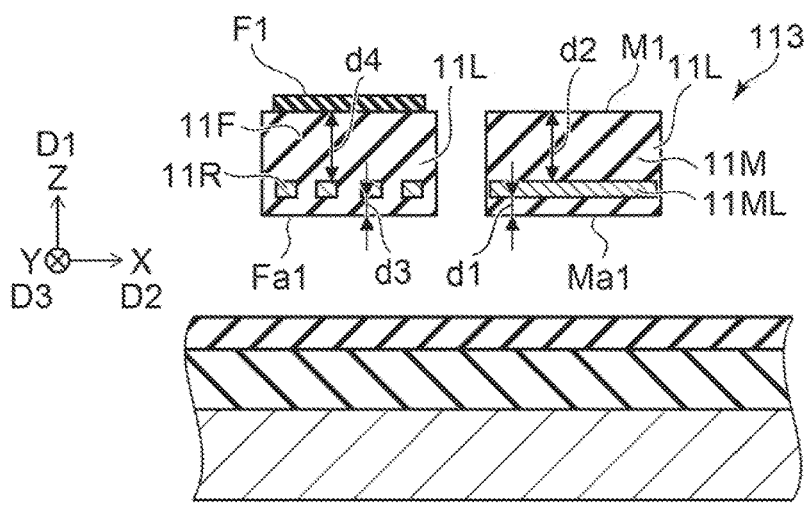
Figure 7C:
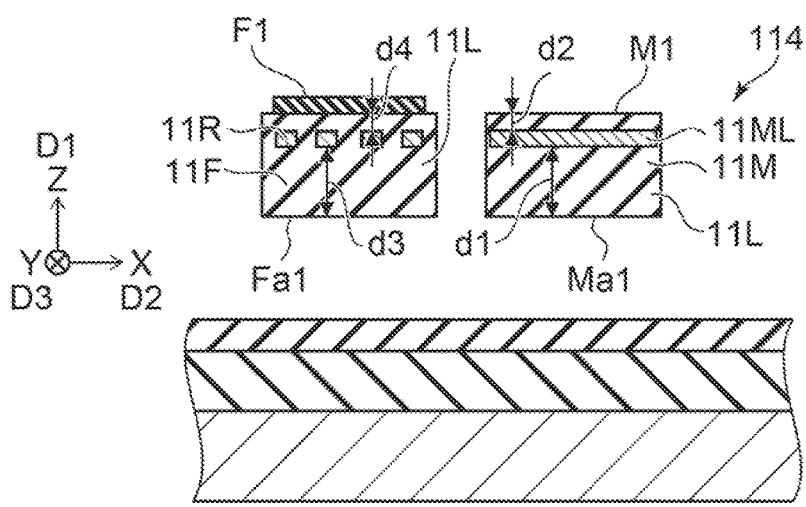

FIGS. 7A to 7C are schematic cross-sectional views illustrating the operation of a sensor according to the first embodiment.

As shown in FIG. 7A, in a sensor 113 according to the embodiment, the first movable electrode 21E is substantially the same layer as the first resistance layer 11R. Except for this, the configuration of the sensor 113 may be the same as that of the sensor 110.

In this example, as shown in FIG. 7B, in the sensor 113, the first distance d1 is shorter than the second distance d2. The third distance d3 is shorter than the fourth distance d4. In this case, the first detection layer 11S is provided on the first deformable surface F1.

As shown in FIG. 7C, in a sensor 114 according to the embodiment, the first distance d1 is longer than the second distance d2. The third distance d3 is longer than the fourth distance d4. The first movable electrode 21E is substantially the same layer as the first resistance layer 11R. Except for this, the configuration of the sensor 114 may be the same as that of the sensor 110. In the sensor 114, the first detection layer 11S may be provided on, for example, the first deformable surface F1.

Figure 8:
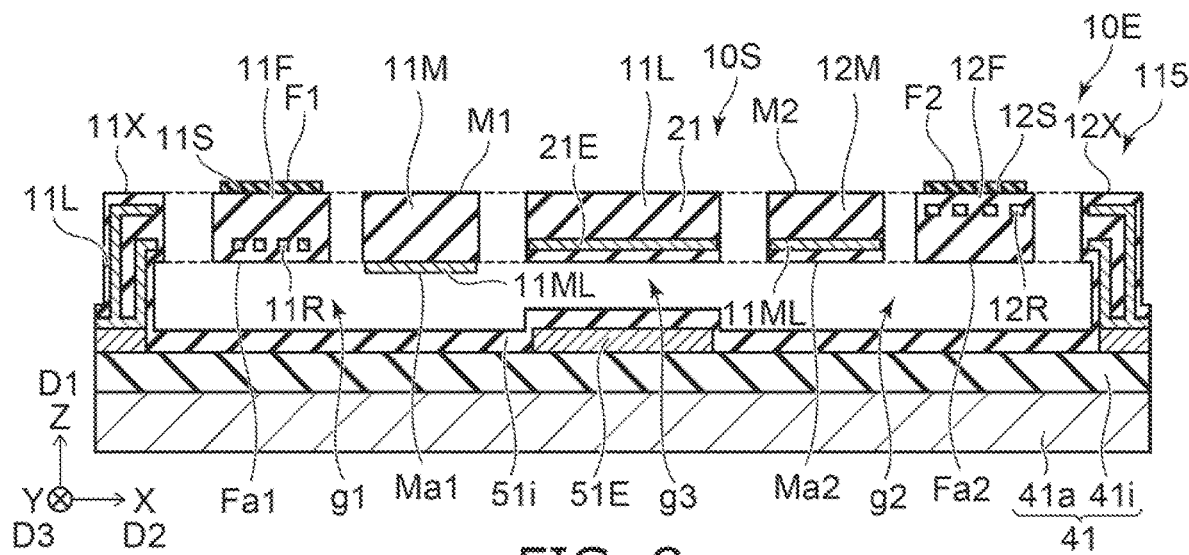
FIG. 8 is a schematic cross-sectional view illustrating a sensor according to the first embodiment.

FIG. 8 is a schematic cross-sectional view illustrating a sensor according to the first embodiment.

As shown in FIG. 8, in a sensor 115 according to the embodiment, the first intermediate conductive layer 11ML of the first intermediate portion 11M is provided on the first intermediate facing surface Ma1. The first detection layer 11S is provided on the first deformable surface F1. Except for this, the configuration of the sensor 115 may be the same as the configuration of the sensor 110. The reverse curvature is effectively obtained. The first intermediate conductive layer 11ML may be, for example, a metal layer or the like.

Figure 9:
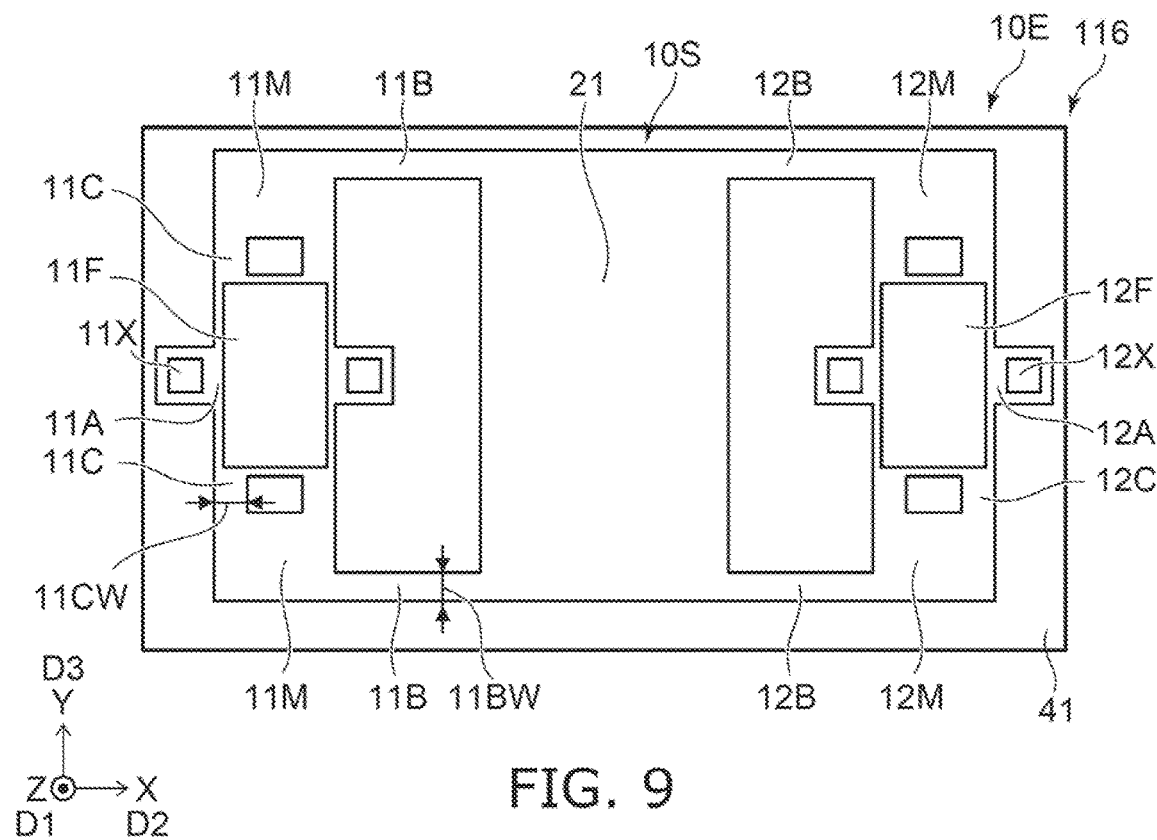
FIG. 9 is a schematic plan view illustrating a sensor according to the first embodiment.

FIG. 9 is a schematic plan view illustrating a sensor according to the first embodiment.

As shown in FIG. 9, in a sensor 116 according to the embodiment, a direction from the first fixed portion 11X to the first deformable portion 11F is along the second direction (X-axis direction). A direction from the first deformable portion 11F to the first intermediate portion 11M is along the third direction D3 (Y-axis direction). In this way, the direction from the first fixed portion 11X to the first deformable portion 11F crosses the direction from the first deformable portion 11F to the first intermediate portion 11M. A direction from the first intermediate portion 11M to the first movable portion 21 is the second direction D2 (X-axis direction). In this way, the direction from the first intermediate portion 11M to the first movable portion 21 crosses the direction from the first deformable portion 11F to the first intermediate portion 11M. As described above, the arrangement of the first fixed portion 11X, the first deformable portion 11F, the first intermediate portion 11M, and the first movable portion 21 can be variously deformed. The configuration of the sensor 116 other than the above may be the same as the configuration of the sensor 110 or the like, for example.

The influence of temperature can also be suppressed in the sensors 111 to 116. According to the embodiment, it is possible to provide a sensor whose characteristics can be improved.

Second Embodiment

In the second embodiment, the sensor is configured to perform a test mode operation in addition to a detection mode operation. The test mode operation is, for example, a self-diagnosis mode operation. This operation may be performed by, for example, a controller 70. In the following, an example of the sensor 110 will be described. The following description can be applied to other sensors (sensors 111 to 116, etc.).

As shown in FIG. 1B, the sensor 110 may include the controller 70. The controller 70 is electrically connected to the first fixed electrode 51E and the first movable electrode 21E. The electrical connection is made, for example, by wirings 75a and 75b.

The controller 70 is configured to perform a first mode operation. The controller 70 is configured to output a first signal sig1 according to the first capacitance between the first fixed electrode 51E and the first movable electrode 21E in the first mode operation. The first capacitance changes depending on the gas included in the space around the first structure body 10S. The first capacitance changes, for example, depending on the concentration of the substance to be detected included in the gas. The first mode operation is the detection mode operation.

The controller 70 may be configured to perform a second mode operation. In the second mode operation, the controller 70 detects the first capacitance while supplying a first current i1 to the first resistance layer 11R (first detection). In the second mode operation, the controller 70 detects the first capacitance without supplying the first current i1 to the first resistance layer 11R (second detection). In the second detection, a current smaller than the first current i1 may be supplied. The controller 70 is configured to output a second signal sig2 based on a difference between the first result in which the first capacitance is detected in the first detection and the second result in which the first capacitance is detected in the second detection. The second signal sig2 includes a signal (information) regarding the presence or absence of abnormality in the sensor element 10E.

In the embodiment, the controller 70 may be configured to output the second signal sig2 regarding to the presence/ absence of abnormality of the sensor element 10E based on the result of detecting the first capacitance while supplying the first current i1 to the first resistance layer 11R in the second mode operation.

In the second mode operation, the first current i1 may be supplied via, for example, a wiring 75c. In the second mode operation, the controller 70 may supply a second current i2 to the second resistance layer 12R (heater). The second current i2 may be supplied, for example, via the wiring 75d (see FIG. 1B).

Figure 10:
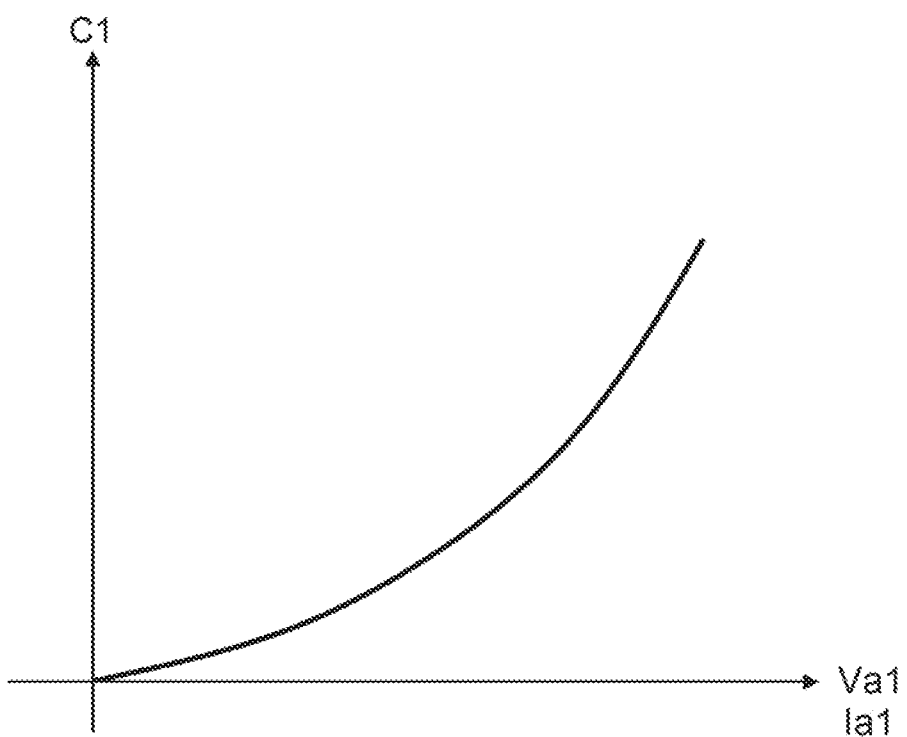
FIG. 10 is a graph illustrating the operation of a sensor according to a second embodiment.

FIG. 10 is a graph illustrating the operation of a sensor according to a second embodiment.

The horizontal axis of FIG. 10 is a current value Ia1 of the first current i1 and the second current i2. The horizontal axis may be a voltage value Va1 corresponding to the current value Ia1. The vertical axis is the first capacitance C1.

For example, when the first current i1 (and the second current i2) is supplied, the temperature of the first deformable portion 11F (and the second deformable portion 12F) rises due to Joule heat, and the first deformable portion 11F (and the second deformable portion 12F) is deformed. At this time, the temperature of the first intermediate portion 11M (and the second intermediate portion 12M) is maintained lower than the temperature of the first deformable portion 11F (and the second deformable portion 12F). Due to the deformation of the deformable portion, the distance between the first fixed electrode 51E and the first movable electrode 21E changes, and the first capacitance C1 changes.

In this example, as the current value Ia1 increases, the first capacitance C1 increases. As the voltage value Va1 increases, the first capacitance C1 increases. Information (design data) regarding the relationship between the current value Ia1 (or voltage value Va1) and the first capacitance C1 may be acquired in advance. By comparing this design data with the measurement results, it is possible to detect anomalies.

Figure 11:
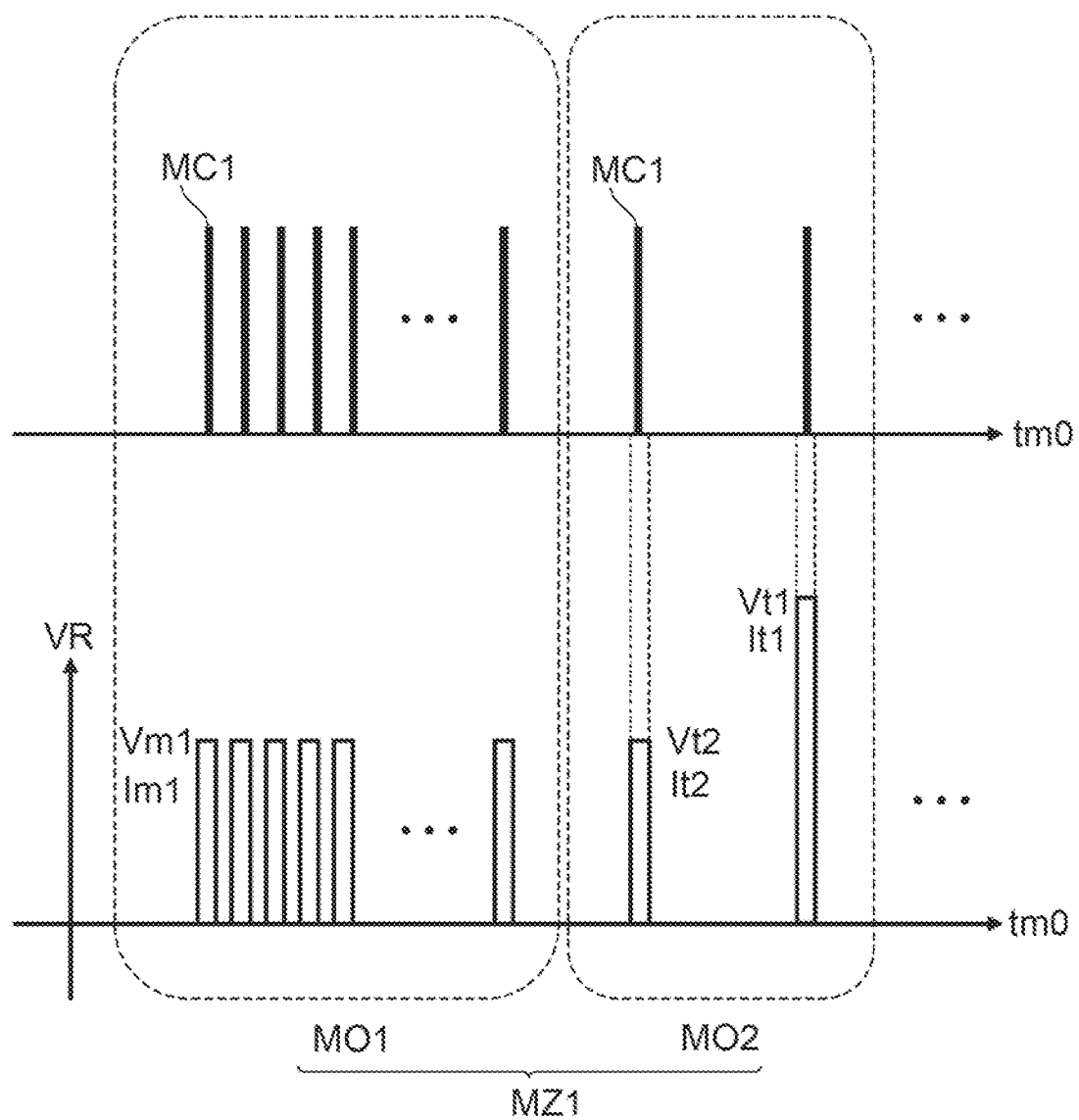
FIG. 11 is a schematic view illustrating the operation of the sensor according to the second embodiment.

FIG. 11 is a schematic view illustrating the operation of the sensor according to the second embodiment.

The horizontal axis of FIG. 11 is time tm0. The vertical axis in the lower figure of FIG. 11 is an applied voltage VR to the resistance layer supplied from the controller 70. The applied voltage VR may be the magnitude of the supplied current.

In the first mode operation MO1, the controller 70 performs measurement MC1 of the first capacitance C1. The measurement MC1 may be repeated. In each of the multiple measurements MC1, a voltage Vm1 (current Im1) may be supplied to the resistance layer from the controller 70. Alternatively, the voltage Vm1 (current Im1) may be supplied to the resistance layer from the controller 70 before or after each of the multiple measurements MC1. As a result, the temperature of the detection layer (first detection layer 11S and second detection layer 12S) rises, and the substance adsorbed on the detection layer can be separated. In the multiple measurements MC1, the characteristics of the detection layer are initialized.

In the second mode operation MO2, a first voltage Vt1 (or first current It1) is supplied to the resistance layer (first resistance layer 11R and second resistance layer 12R) by the controller 70. In this state, the measurement MC1 of the first capacitance C1 is performed. This measurement MC1 corresponds to the first detection.

In this example, in the second mode operation MO2, a second voltage Vt2 (or second current It2) is supplied to the resistance layer (first resistance layer 11R and second resistance layer 12R) by the controller 70. In this state, the measurement MC1 of the first capacitance C1 is performed. This measurement MC1 corresponds to the second detection. In the second detection, the second voltage Vt2 (or second current It2) may be substantially zero. The controller 70 outputs the second signal sig2 based on the difference between the result of the first detection and the result of the first detection.

The controller 70 may repeatedly performs a set MZ1 of the first mode operation MO1 and the second mode operation MO2.

Figure 12:
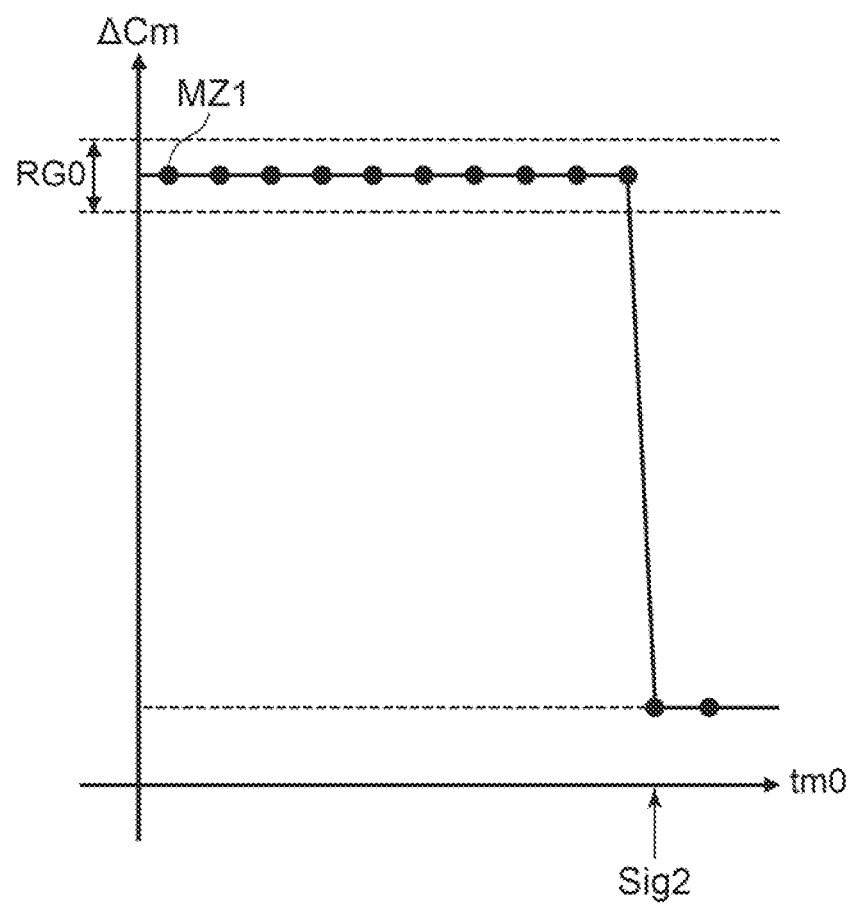
FIG. 12 is a schematic view illustrating the operation of the sensor according to the second embodiment.

FIG. 12 is a schematic view illustrating the operation of the sensor according to the second embodiment.

The horizontal axis of FIG. 12 is time tm0. The vertical axis of FIG. 12 is a difference ΔCm between the value detected by the first detection and the value detected by the second detection. As shown in FIG. 12, the detection results of each of the multiple sets MZ1 are plotted. For example, a reference value RG0 is provided for the difference ΔCm. If the measured value of the difference ΔCm is within the reference value RG0, it is determined that there is no abnormality. When the measured value of the difference ΔCm deviates from the reference value RG0, it is determined that there is an abnormality. In this case, the second signal sig2 of "abnormality" is output from the controller 70 in the sensor element 10E.

Figure 13:
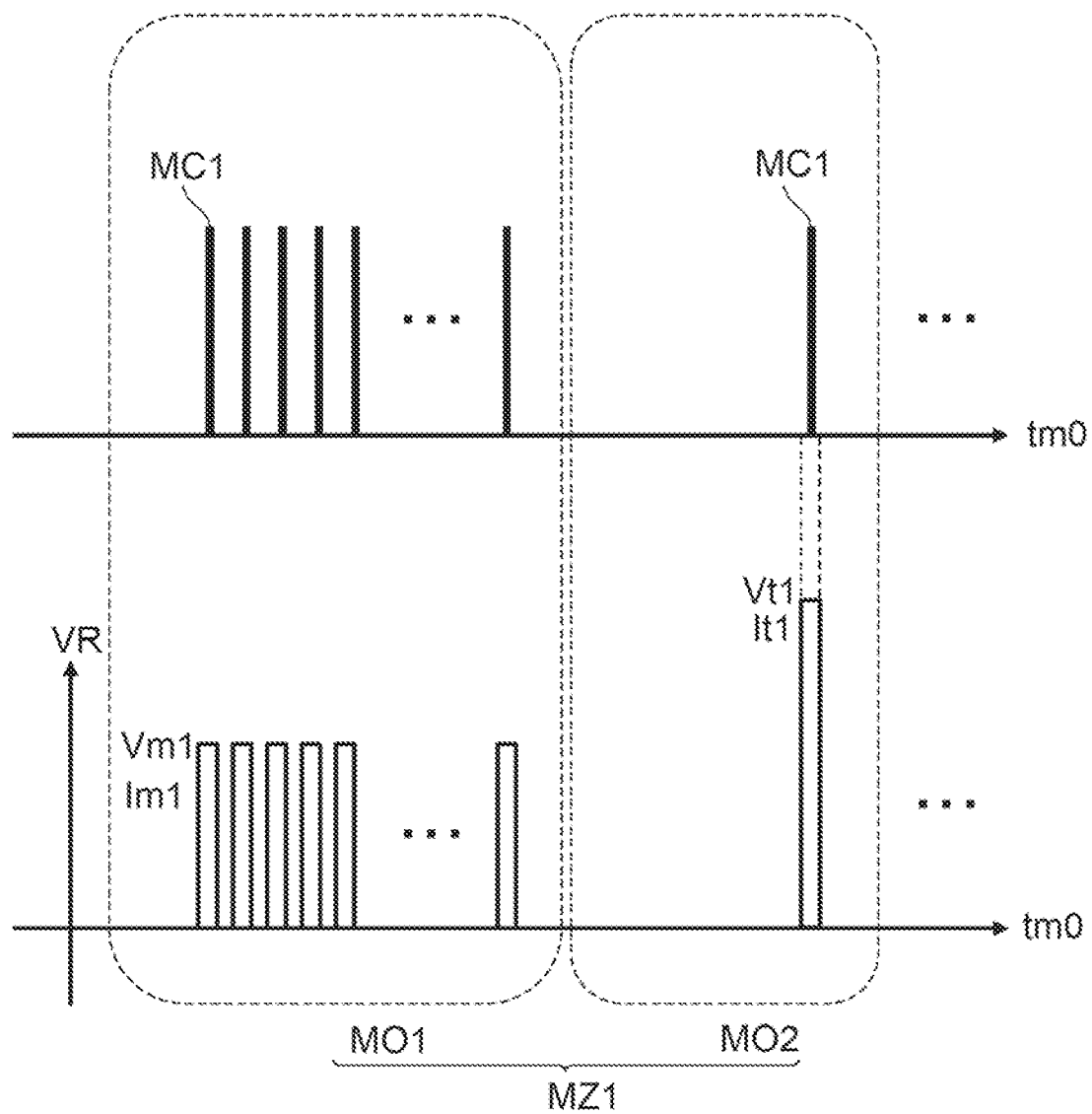
FIG. 13 is a schematic view illustrating the operation of the sensor according to the second embodiment.

FIG. 13 is a schematic view illustrating the operation of the sensor according to the second embodiment.

Also in the example of FIG. 13, in the first mode operation MO1, the measurement MC1 of the first capacitance C1 is performed by the controller 70. The measurement MC1 may be repeated. In each of the multiple measurements MC1, the voltage Vm1 (current Im1) may be supplied to the resistance layer from the controller 70. Alternatively, the voltage Vm1

(current Im1) may be supplied to the resistance layer from the controller 70 before or after each of the multiple measurements MC1.

In the second mode operation MO2, the first voltage Vt1 (or first current It1) is supplied to the resistance layer (first resistance layer 11R and second resistance layer 12R) by the controller 70. In this state, the measurement MC1 of the first capacitance C1 is performed. In this example, the controller 70 outputs a second signal sig2 regarding the presence or absence of an abnormality in the sensor element 10E based on the detection result. The controller 70 may repeatedly perform the set MZ1 of the first mode operation MO1 and the second mode operation MO2.

Figure 14:
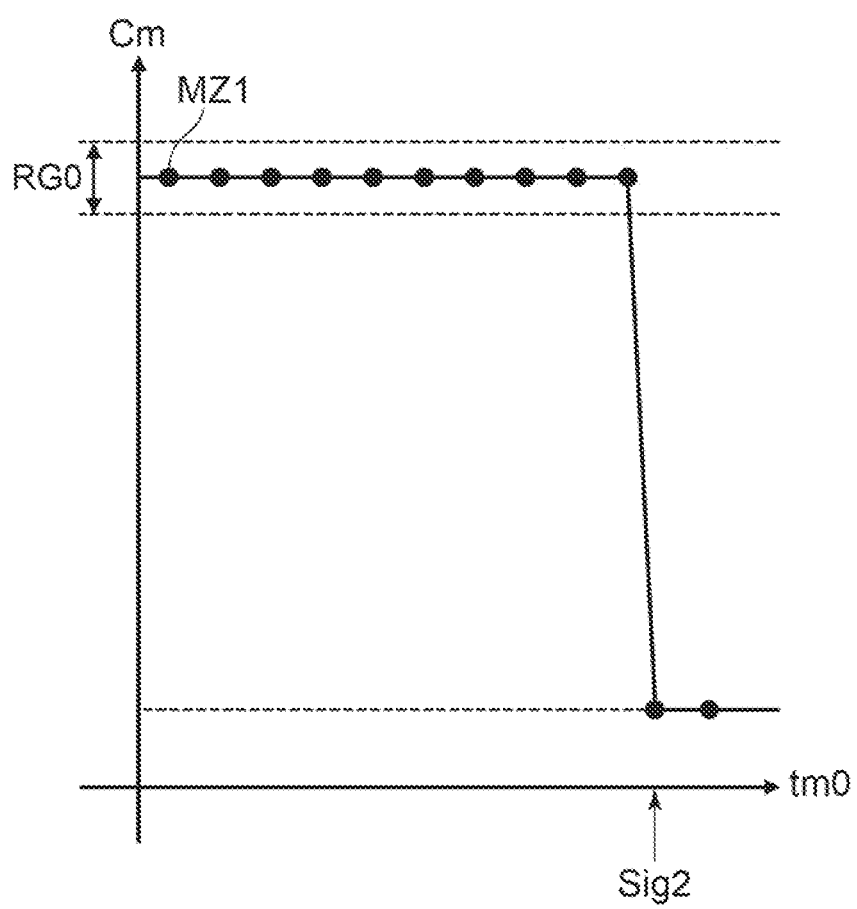
FIG. 14 is a schematic view illustrating the operation of the sensor according to the second embodiment.

FIG. 14 is a schematic view illustrating the operation of the sensor according to the second embodiment.

The horizontal axis of FIG. 14 is time tm0. The vertical axis of FIG. 14 is the measured value Cm by the measurement MC1 of the first capacitance C1. As shown in FIG. 14, the detection results of each of the multiple sets MZ1 are plotted. For example, the reference value RG0 is provided for the measured value Cm. If the measured value Cm is within the reference value RG0, it is determined that there is no abnormality. When the measured value Cm deviates from the reference value RG0, it is determined that there is an abnormality. In this case, the second signal sig2 of "abnormality" is output from the controller 70 in the sensor element 10E.

Figure 15:
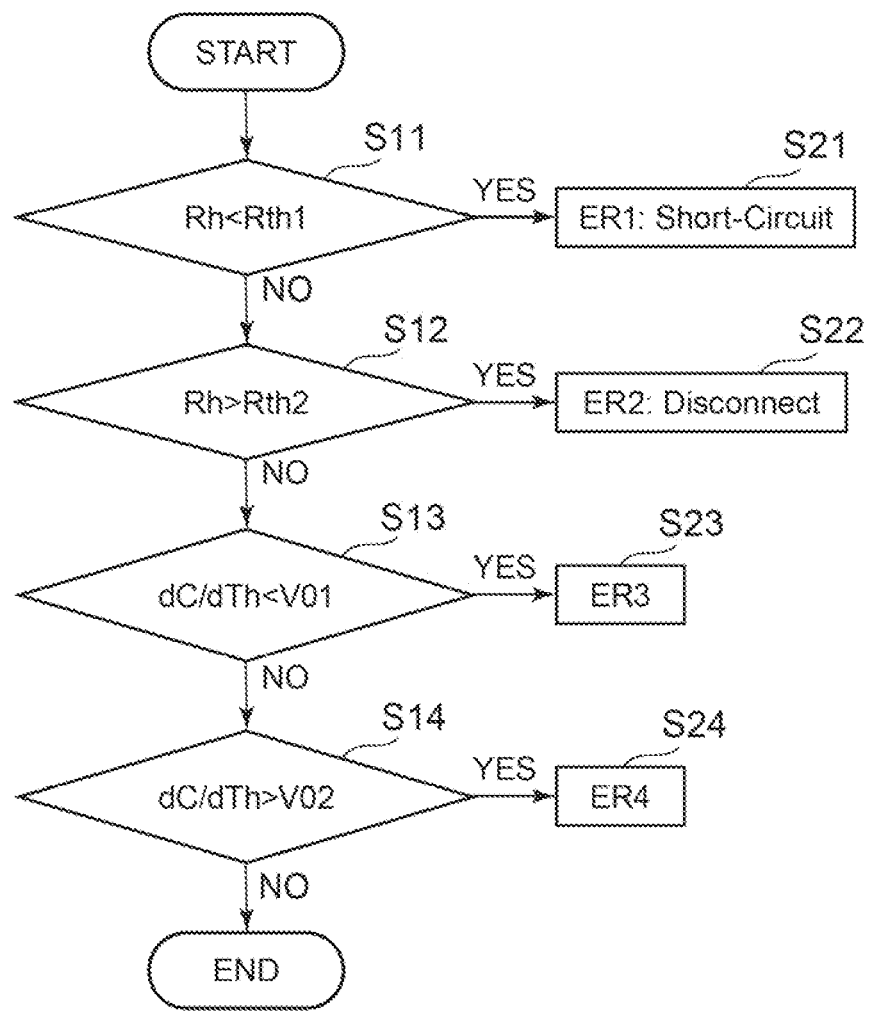
FIG. 15 is a schematic view illustrating the operation of the sensor according to the second embodiment.

FIG. 15 is a schematic view illustrating the operation of the sensor according to the second embodiment.

FIG. 15 shows an example of processing that is configured to be performed by the controller 70.

For example, a resistance Rh of the resistance layer (first resistance layer 11R and second resistance layer 12R) is compared with a reference value Rth1 (step S11). When the resistance Rh is lower than the reference value Rth1, it is determined as an error ER1 (step S21). The error ER1 corresponds to "circuit short".

If the resistance Rh is not lower than the reference value Rth1, the process proceeds to step S12. In step S12, the resistance Rh is compared with a reference value Rth2. When the resistance Rh is higher than the reference value Rth2, it is determined as an error ER2 (step S22). The error ER2 corresponds to "disconnection".

If the resistance Rh is not higher than the reference value Rth2, the process proceeds to step S13. In step S13, a ratio dC/dTh is compared with a reference value V01. The ratio dC/dTh is a ratio of the change (dC) of the first capacitance C1 to the change of temperature (dTh). This change in temperature (dTh) is a change in temperature due to application of voltage (or supply of current) to the heaters (first resistance layer 11R and second resistance layer 12R). The change in temperature in this case is not a change in the temperature of the environment. When the ratio dC/dTh is lower than the reference value V01, it is determined as an error ER3 (step S23). The error ER3 corresponds to the "decrease in ratio". "Decrease in ratio" is one example of anomalies. Instead of comparing the ratio dC/dTh with the reference value V01, for example, the difference ΔCm may be compared with the reference value. Instead of comparing the ratio dC/dTh with the reference value V01, for example, the measured value Cm may be compared with the reference value.

If the ratio dC/dTh is not lower than the reference value V01, the process proceeds to step S14. In step S14, the ratio dC/dTh is compared with a reference value V02. When the ratio dC/dTh is higher than the reference value V02, it is determined as an error ER4 (step S24). The error ER4 corresponds to the "increase in ratio". "Increase in ratio" is one example of anomalies.

If the ratio dC/dTh is not higher than the reference value V02, the process ends. In this case, it is determined that there is no abnormality.

Figure 16:
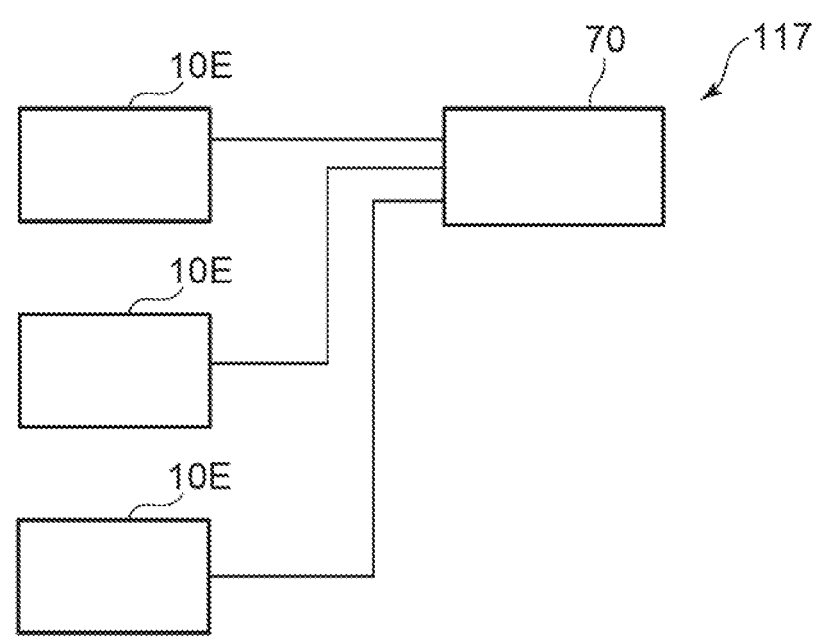
FIG. 16 is a schematic view illustrating a sensor according to the second embodiment.

FIG. 16 is a schematic view illustrating a sensor according to the second embodiment.

As shown in FIG. 16, a sensor 117 according to the embodiment includes multiple sensor elements 10E. For example, the first mode operation MO1 and the second mode operation MO2 described above are performed using one of the multiple sensor elements 10E. For example, in the second mode operation MO2, when the second signal sig2 indicates that there is an abnormality with respect to one of the multiple sensor elements 10E, the controller 70 is configured to perform the first mode operation MO1 with respect to another one of the multiple sensor elements 10E. The first mode operation MO1 and the second mode operation MO2 may be repeatedly performed with respect to the other one of the multiple sensor elements 10E.

By providing the multiple sensor elements 10E, if an abnormality occurs in one sensor element 10E, detection can be continuously performed by another sensor element 10E.

Figure 17A:
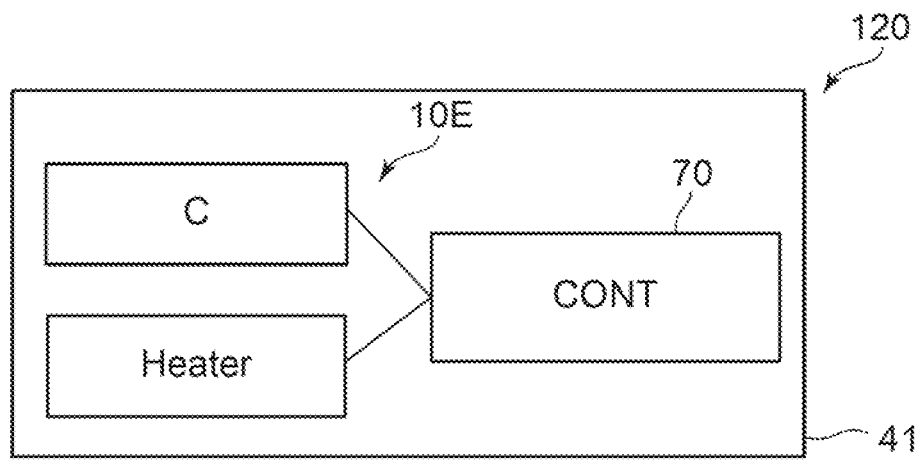
FIGS. 17A and 17B are schematic views illustrating sensors according to the second embodiment.
Figure 17B:
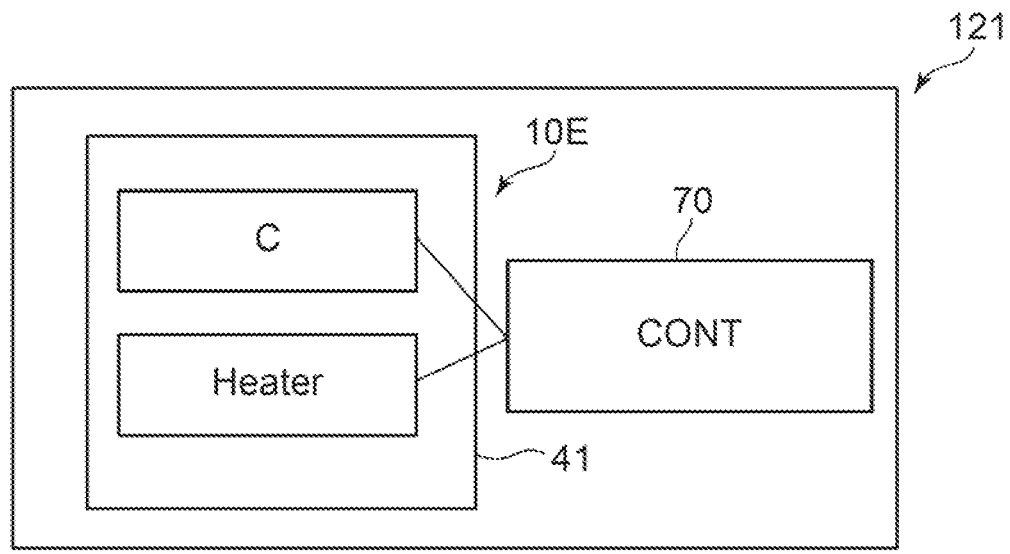

FIGS. 17A and 17B are schematic views illustrating sensors according to the second embodiment.

As shown in FIG. 17A, in a sensor 120, the controller 70 is provided on the first base body 41 of the sensor element 10E. The controller 70 may include, for example, a circuit (for example, CMOS: complementary metal oxide semiconductor or the like) formed in a part of the first base body 41.

As shown in FIG. 17B, a sensor 121 may be provided with the controller 70 separately from the first base body 41 of the sensor element 10E. The controller 70 may include, for example, a microcomputer or the like.

Third Embodiment

The third embodiment relates to a capacitor device.

Figure 18A:
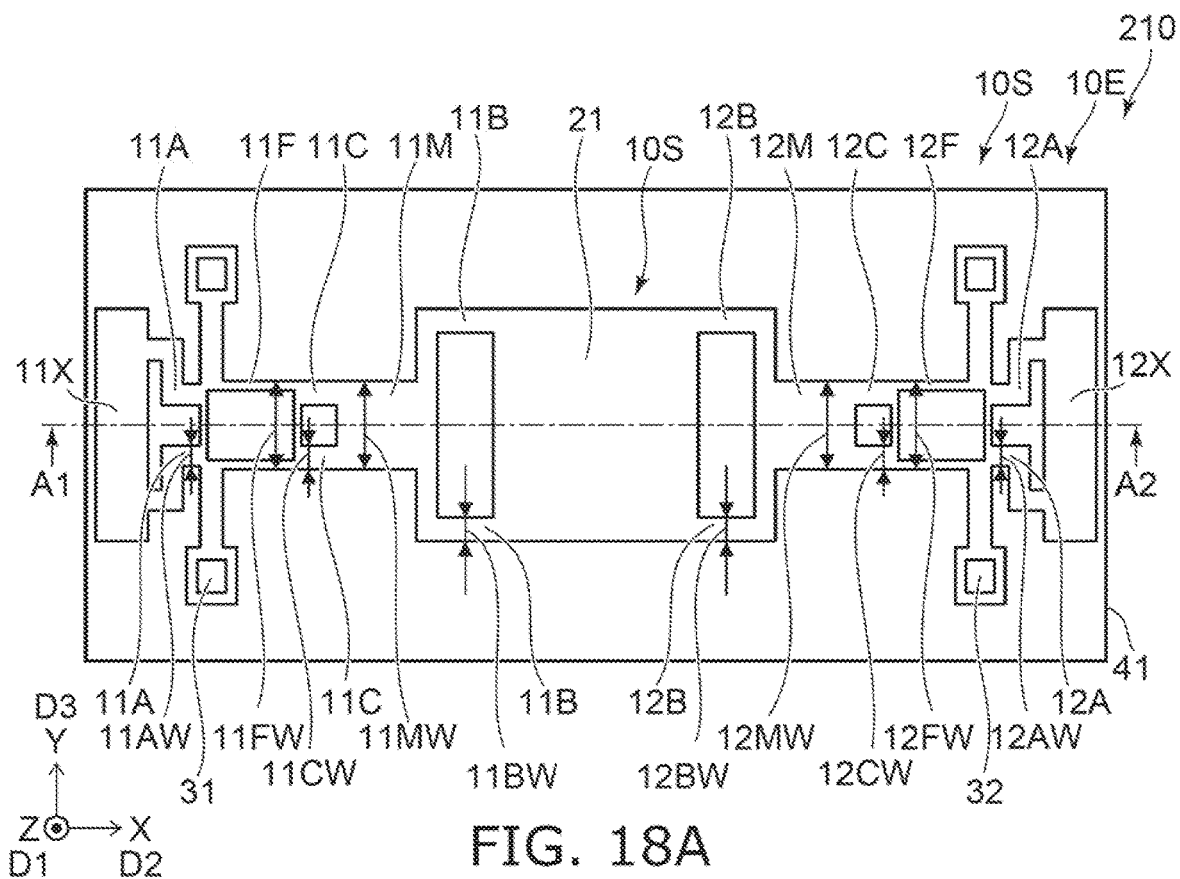
FIGS. 18A and 18B are schematic views illustrating a capacitor device according to a third embodiment.
Figure 18B:
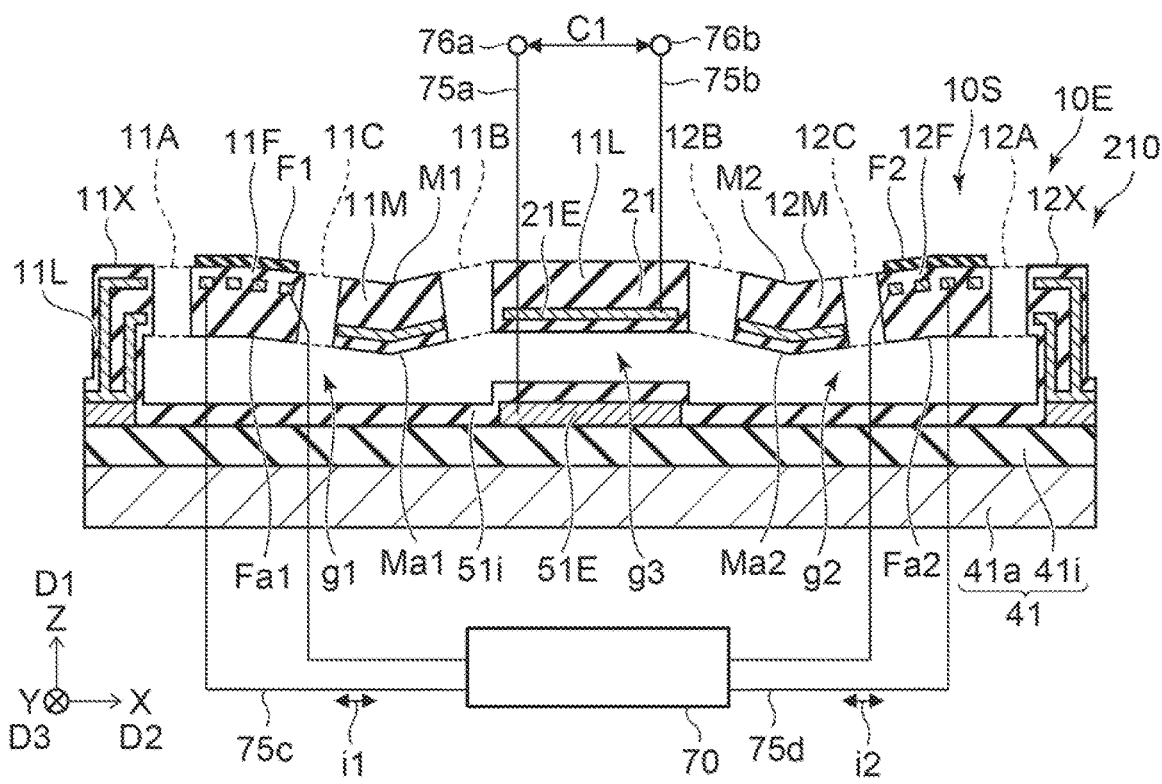

FIGS. 18A and 18B are schematic views illustrating a capacitor device according to a third embodiment.

FIG. 18A is a plan view. FIG. 18B is a cross-sectional view taken along the line A1-A2 of FIG. 18A.

As shown in FIGS. 18A and 18B, a capacitor device 210 according to the embodiment includes the sensor element 10E. The sensor element 10E includes the first base body 41, the first fixed electrode 51E, and the first structure body 10S. The first fixed electrode 51E is fixed to the first base body 41.

The first structure body 10S includes the first fixed portion 11X fixed to the first base body 41, the first deformable portion 11F supported by the first fixed portion 11X, the first intermediate portion supported by the first deformable portion 11F, and the first movable portion 21 supported by the first intermediate portion 11M. The first deformable portion 11F includes the first resistance layer 11R. The first movable portion 21 includes the first movable electrode 21E facing the first fixed electrode 51E.

The first gap g1 is provided between the first base body 41 and the first deformable portion 11F, and between the first base body 41 and the first intermediate portion 11M. The third gap g3 is provided between the first fixed electrode 51E and the first movable electrode 21E.

The first deformable portion 11F includes a first deformed facing surface Fa1 facing the first base body 41 and a first deformable surface F1. The first deformed facing surface Fa1 is between the first base body 41 and the first deformable surface F1 in the first direction D1 from the first base body 41 to the first movable portion 21.

The first intermediate portion 11M includes the first intermediate facing surface Ma1 facing the first base body 41 and the first intermediate surface M1. The first intermediate facing surface Ma1 is between the first base body 41 and the first intermediate surface M1 in the first direction D1.

As the temperature rises, the first deformable surface F1 is deformed into one of the concave shape or the convex shape, and the first intermediate surface M1 is deformed into the other of the concave shape and the convex shape.

The controller 70 is configured to change the first capacitance C1 between the first fixed electrode 51E and the first movable electrode 21E by supplying a current to the first resistance layer 11R.

For example, terminals 76a and 76b may be provided. The terminal 76a is electrically connected to the first fixed electrode 51E by the wiring 75a. The terminal 76b is electrically connected to the first movable electrode 21E by the wiring 75b. The first capacitance C1 is generated between these terminals. The first deformable portion 11F is deformed by the current supplied to the first resistance layer 11R, and the distance between the first fixed electrode 51E and the first movable electrode 21E changes. As a result, the first capacitance C1 is changed.

In the embodiment, the above-mentioned first intermediate portion 11M is provided. As a result, the influence of changes in ambient temperature can be suppressed. The first capacitance C1 can be controlled with high accuracy.

The sensor configuration described with respect to the first embodiment may be applied to the capacitor device according to the third embodiment.

The embodiments include the following configurations (e.g., technical proposals).

Configuration 1
  A sensor, comprising:
  a sensor element including
  a first base body,
  a first fixed electrode fixed to the first base body, and
  a first structure body,
  the first structure body including
  a first fixed portion fixed to the first base body,
  a first deformable portion supported by the first fixed portion,
  a first intermediate portion supported by the first deformable portion, and
  a first movable portion supported by the first intermediate portion, the first movable portion including a first movable electrode facing the first fixed electrode,
  a first gap being provided between the first base body and the first deformable portion, and between the first base body and the first intermediate portion,
  a third gap being provided between the first fixed electrode and the first movable electrode,
  the first deformable portion including a first deformed facing surface facing the first base body, and a first deformable surface, the first deformed facing surface being between the first base body and the first deformable surface in a first direction from the first base body to the first movable portion,
  the first intermediate portion including a first intermediate facing surface facing the first base body, and a first intermediate surface, the first intermediate facing surface being between the first base body and the first intermediate surface in the first direction,
  the first deformable surface being possible to be deformed depending on a gas included in a space around the first structure body, and
  with a rise of a temperature, the first deformable surface deforming into one of a concave shape and a convex shape, and the first intermediate surface deforming into an other of the concave shape and the convex shape.

Configuration 2
  The sensor according to Configuration 1, wherein
  the first structure body includes a first connection portion connecting the first deformable portion and the first intermediate portion,
  a first connection direction from the first deformable portion to the first intermediate portion crosses the first direction,
  a width of at least a part of the first connection portion along a first connection crossing direction is narrower than a width of the first intermediate portion along the first connection crossing direction, and
  the first connection crossing direction crosses a plane including the first direction and the first connection direction.

Configuration 3
  The sensor according to Configuration 1, wherein
  the first structure body includes a first movable connection portion connecting the first intermediate portion and the first movable portion,
  a first movable connection direction from the first intermediate portion to the first movable portion crosses the first direction,
  a width of at least a part of the first movable connection portion along the first movable connection crossing direction is narrower than a width of the first intermediate portion along the first movable connection crossing direction, and
  the first movable connection crossing direction crosses a plane including the first direction and the first movable connection direction.

Configuration 4
  The sensor according to Configuration 1, wherein
  the first structure body includes a first fixed connection portion connecting the first fixed portion and the first deformable portion,
  the first fixed connection direction from the first fixed portion to the first deformable portion crosses the first direction,
  a width of at least a part of the first fixed connection portion along the first fixed connection crossing direction is narrower than a width of the first deformable portion along the first fixed connection crossing direction, and
  the first fixed connection crossing direction crosses a plane including the first direction and the first fixed connection direction.

Configuration 5
  The sensor according to Configuration 1, wherein
  the first deformable portion is between the first fixed portion and the first movable portion, and
  the first intermediate portion is between the first deformable portion and the first movable portion.

Configuration 6
  The sensor according to Configuration 1, wherein
  a direction from the first fixed portion to the first deformable portion crosses a direction from the first deformable portion to the first intermediate portion, and
  a direction from the first intermediate portion to the first movable portion crosses the direction from the first deformable portion to the first intermediate portion.

Configuration 7
The sensor according to Configuration 1, wherein
the first deformable portion includes
a first resistance layer and
a first detection layer,
the first detection layer being possible to be deformed depending on the gas.

Configuration 8
The sensor according to Configuration 7, wherein
at least a part of the first detection layer overlaps the first resistance layer in the first direction.

Configuration 9
The sensor according to Configuration 7, wherein
the first intermediate portion includes a first intermediate conductive layer,
a first distance along the first direction between the first intermediate conductive layer and the first intermediate facing surface is shorter than a second distance along the first direction between the first intermediate conductive layer and the first intermediate surface, a third distance along the first direction between the first resistance layer and the first deformed facing surface is longer than a fourth distance along the first direction between the first resistance layer and the first deformable surface, alternatively the first distance is longer than the second distance, and the third distance is shorter than the fourth distance.

Configuration 10
The sensor according to Configuration 7, wherein
the first intermediate portion includes a first intermediate conductive layer,
a first distance along the first direction between the first intermediate conductive layer and the first intermediate facing surface is longer than a second distance along the first direction between the first intermediate conductive layer and the first intermediate surface, and the first resistance layer is between the first base body and the first detection layer, alternatively
the first distance is shorter than the second distance, and the first detection layer is between the first base body and the first resistance layer.

Configuration 11
The sensor according to Configuration 7, wherein
the first intermediate portion includes a first intermediate conductive layer,
the first intermediate conductive layer is provided on the first intermediate facing surface, and
the first detection layer is provided on the first deformable surface.

Configuration 12
The sensor according to Configuration 7, wherein
the first structure body further includes
a second fixed portion fixed to the first base body,
a first deformable portion supported by the second fixed portion, and
a second intermediate portion supported by the second deformable portion,
the first movable portion is supported by the first intermediate portion and the second intermediate portion,
a second gap is provided between the first base body and the second deformable portion and between the first base body and the second intermediate portion,
the second deformable portion includes a second deformed facing surface facing the first base body, and a second deformable surface, the second deformed facing surface is between the first base body and the second deformable surface in the first direction,
the second intermediate portion includes a second intermediate facing surface facing the first base body, and a second intermediate surface, the second intermediate facing surface is between the first base body and the second intermediate surface in the first direction,
the second deformable surface is possible to be deformed depending on a gas included in the space, and
with the rise of the temperature, the second deformable surface is deformed into the one of the concave shape or the convex shape, the first intermediate surface is deformed into the other of the concave shape or the convex shape.

Configuration 13
The sensor according to Configuration 12, wherein
the first movable portion is between the first intermediate portion and the second intermediate portion.

Configuration 14
The sensor according to Configuration 12, wherein
the first structure body includes a second connection portion connecting the second deformable portion and the second intermediate portion,
a second connection direction from the second deformable portion to the second intermediate portion crosses the first direction,
a width of at least a part of the second connection portion along a second connection crossing direction is narrower than a width of the second intermediate portion along the second connection crossing direction, and
the second connection crossing direction crosses a plane including the first direction and the second connection direction.

Configuration 15
The sensor according to Configuration 7, further comprising:
a controller,
the controller being configured to perform a first mode operation,
the controller being configured to output a first signal corresponding to a first capacitance between the first fixed electrode and the first movable electrode in the first mode operation, and
the first capacitance changing depending on the gas included in the space.

Configuration 16
The sensor according to Configuration 15, wherein
the controller is configured to perform a second mode operation, and
in the second mode operation, the controller is configured to output a second signal regarding presence or absence of abnormality in the sensor element based on a difference between a first result obtained by detecting the first capacitance while supplying a first current to the first resistance layer and a second result obtained by detecting the first capacitance without supplying the first current to the first resistance layer.

Configuration 17
The sensor according to Configuration 15, wherein
the controller is configured to perform a second mode operation, and
in the second mode operation, the controller is configured to output a second signal regarding presence or absence of abnormality in the sensor element based on a result obtained by detecting the first capacitance while supplying a first current to the first resistance layer.

Configuration 18
The sensor according to Configuration 15, wherein
the controller is provided on the first base body.

Configuration 19

The sensor according to Configuration 16, comprising:
a plurality of the sensor elements,
in the second mode operation, when the second signal indicates that there is an abnormality with respect to one of the sensor elements, the controller is configured to perform the first mode operation with respect to another one of the sensor elements.

Configuration 20

A capacitor device, comprising:
a first base body;
a first fixed electrode fixed to the first base body;
a first structure body; and
a controller,
the first structure body including
a first fixed portion fixed to the first base body,
a first deformable portion supported by the first fixed portion, the first deformable portion including a first resistance layer,
a first intermediate portion supported by the first deformable portion, and
a first movable portion supported by the first deformable portion, the first movable portion including a first movable electrode facing the first fixed electrode,
a first gap being provided between the first base body and the first deformable portion and between the first base body and the first intermediate portion,
a third gap being provided between the first fixed electrode and the first movable electrode,
the first deformable portion including a first deformed facing surface facing the first base body, and a first deformable surface, the first deformed facing surface being between the first base body and the first deformable surface in a first direction from the first base body to the first movable portion,
the first intermediate portion including a first intermediate facing surface facing the first base body, and a first intermediate surface,
the first intermediate facing surface being between the first base body and the first intermediate surface in the first direction,
with a rise of a temperature, the first deformable surface being deformed into one of a concave shape or a convex shape, the first intermediate surface being deformed into an other of the concave shape or the convex shape, and
the controller being configured to change a first capacitance between the first fixed electrode and the first movable electrode by supplying a current to the first resistance layer.

According to the embodiments, it is possible to provide a sensor and a capacitor device whose characteristics can be improved.

In the specification, a state of being electrically connected includes not only the case of being directly contacted and connected, but also the case of being connected via another conductive member or the like.

In the specification of the application, "perpendicular" and "parallel" refer to not only strictly perpendicular and strictly parallel but also include, for example, the fluctuation due to manufacturing processes, etc. It is sufficient to be substantially perpendicular and substantially parallel.

Hereinabove, exemplary embodiments of the invention are described with reference to specific examples. However, the embodiments of the invention are not limited to these specific examples. For example, one skilled in the art may similarly practice the invention by appropriately selecting specific configurations of components included in sensors and capacitor devices such as base bodies, structure bodies, supporters, deformable portions, intermediate portion, movable portions, fixed electrodes, controllers, etc., from known art. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all sensors, and capacitor devices practicable by an appropriate design modification by one skilled in the art based on the sensors, and the capacitor devices described above as embodiments of the invention also are within the scope of the invention to the extent that the purport of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. A sensor, comprising:
a sensor element including
a first base body,
a first fixed electrode fixed to the first base body, and
a first structure body,
the first structure body including
a first fixed portion fixed to the first base body,
a first deformable portion supported by the first fixed portion,
a first intermediate portion supported by the first deformable portion, and
a first movable portion supported by the first intermediate portion, the first movable portion including a first movable electrode facing the first fixed electrode,
a first gap being provided between the first base body and the first deformable portion, and between the first base body and the first intermediate portion,
a third gap being provided between the first fixed electrode and the first movable electrode,
the first deformable portion including a first deformed facing surface facing the first base body, and a first deformable surface, the first deformed facing surface being between the first base body and the first deformable surface in a first direction from the first base body to the first movable portion,
the first intermediate portion including a first intermediate facing surface facing the first base body, and a first intermediate surface, the first intermediate facing surface being between the first base body and the first intermediate surface in the first direction,
the first deformable surface being possible to be deformed depending on a gas included in a space around the first structure body, and
with a rise of a temperature, the first deformable surface deforming into one of a concave shape and a convex shape, and the first intermediate surface deforming into an other of the concave shape and the convex shape.

2. The sensor according to claim 1, wherein
the first structure body includes a first connection portion connecting the first deformable portion and the first intermediate portion,
a first connection direction from the first deformable portion to the first intermediate portion crosses the first direction,
a width of at least a part of the first connection portion along a first connection crossing direction is narrower than a width of the first intermediate portion along the first connection crossing direction, and
the first connection crossing direction crosses a plane including the first direction and the first connection direction.

3. The sensor according to claim 1, wherein
the first structure body includes a first movable connection portion connecting the first intermediate portion and the first movable portion,
a first movable connection direction from the first intermediate portion to the first movable portion crosses the first direction,
a width of at least a part of the first movable connection portion along the first movable connection crossing direction is narrower than a width of the first intermediate portion along the first movable connection crossing direction, and
the first movable connection crossing direction crosses a plane including the first direction and the first movable connection direction.

4. The sensor according to claim 1, wherein
the first structure body includes a first fixed connection portion connecting the first fixed portion and the first deformable portion,
the first fixed connection direction from the first fixed portion to the first deformable portion crosses the first direction,
a width of at least a part of the first fixed connection portion along the first fixed connection crossing direction is narrower than a width of the first deformable portion along the first fixed connection crossing direction, and
the first fixed connection crossing direction crosses a plane including the first direction and the first fixed connection direction.

5. The sensor according to claim 1, wherein
the first deformable portion is between the first fixed portion and the first movable portion, and
the first intermediate portion is between the first deformable portion and the first movable portion.

6. The sensor according to claim 1, wherein
a direction from the first fixed portion to the first deformable portion crosses a direction from the first deformable portion to the first intermediate portion, and
a direction from the first intermediate portion to the first movable portion crosses the direction from the first deformable portion to the first intermediate portion.

7. The sensor according to claim 1, wherein
the first deformable portion includes
a first resistance layer and
a first detection layer,
the first detection layer being possible to be deformed depending on the gas.

8. The sensor according to claim 7, wherein
at least a part of the first detection layer overlaps the first resistance layer in the first direction.

9. The sensor according to claim 7, wherein
the first intermediate portion includes a first intermediate conductive layer,
a first distance along the first direction between the first intermediate conductive layer and the first intermediate facing surface is shorter than a second distance along the first direction between the first intermediate conductive layer and the first intermediate surface, a third distance along the first direction between the first resistance layer and the first deformed facing surface is longer than a fourth distance along the first direction between the first resistance layer and the first deformable surface, alternatively the first distance is longer than the second distance, and the third distance is shorter than the fourth distance.

10. The sensor according to claim 7, wherein
the first intermediate portion includes a first intermediate conductive layer,
a first distance along the first direction between the first intermediate conductive layer and the first intermediate facing surface is longer than a second distance along the first direction between the first intermediate conductive layer and the first intermediate surface, and the first resistance layer is between the first base body and the first detection layer, alternatively
the first distance is shorter than the second distance, and the first detection layer is between the first base body and the first resistance layer.

11. The sensor according to claim 7, wherein
the first intermediate portion includes a first intermediate conductive layer,
the first intermediate conductive layer is provided on the first intermediate facing surface, and
the first detection layer is provided on the first deformable surface.

12. The sensor according to claim 7, wherein
the first structure body further includes
a second fixed portion fixed to the first base body,
a first deformable portion supported by the second fixed portion, and
a second intermediate portion supported by the second deformable portion,
the first movable portion is supported by the first intermediate portion and the second intermediate portion,
a second gap is provided between the first base body and the second deformable portion and between the first base body and the second intermediate portion,
the second deformable portion includes a second deformed facing surface facing the first base body, and a second deformable surface, the second deformed facing surface is between the first base body and the second deformable surface in the first direction,
the second intermediate portion includes a second intermediate facing surface facing the first base body, and a second intermediate surface, the second intermediate facing surface is between the first base body and the second intermediate surface in the first direction,
the second deformable surface is possible to be deformed depending on a gas included in the space, and
with the rise of the temperature, the second deformable surface is deformed into the one of the concave shape or the convex shape, the first intermediate surface is deformed into the other of the concave shape or the convex shape.

13. The sensor according to claim 12, wherein
the first movable portion is between the first intermediate portion and the second intermediate portion.

14. The sensor according to claim 12, wherein
the first structure body includes a second connection portion connecting the second deformable portion and the second intermediate portion,
a second connection direction from the second deformable portion to the second intermediate portion crosses the first direction,
a width of at least a part of the second connection portion along a second connection crossing direction is narrower than a width of the second intermediate portion along the second connection crossing direction, and
the second connection crossing direction crosses a plane including the first direction and the second connection direction.

15. The sensor according to claim 7, further comprising:
a controller,
the controller being configured to perform a first mode operation,
the controller being configured to output a first signal corresponding to a first capacitance between the first fixed electrode and the first movable electrode in the first mode operation, and
the first capacitance changing depending on the gas included in the space.

16. The sensor according to claim 15, wherein
the controller is configured to perform a second mode operation, and
in the second mode operation, the controller is configured to output a second signal regarding presence or absence of abnormality in the sensor element based on a difference between a first result obtained by detecting the first capacitance while supplying a first current to the first resistance layer and a second result obtained by detecting the first capacitance without supplying the first current to the first resistance layer.

17. The sensor according to claim 15, wherein
the controller is configured to perform a second mode operation, and
in the second mode operation, the controller is configured to output a second signal regarding presence or absence of abnormality in the sensor element based on a result obtained by detecting the first capacitance while supplying a first current to the first resistance layer.

18. The sensor according to claim 15, wherein
the controller is provided on the first base body.

19. The sensor according to claim 16, comprising:
a plurality of the sensor elements,
in the second mode operation, when the second signal indicates that there is an abnormality with respect to one of the sensor elements, the controller is configured to perform the first mode operation with respect to another one of the sensor elements.

20. A capacitor device, comprising:
a first base body;
a first fixed electrode fixed to the first base body;
a first structure body; and
a controller,
the first structure body including
a first fixed portion fixed to the first base body,
a first deformable portion supported by the first fixed portion, the first deformable portion including a first resistance layer,
a first intermediate portion supported by the first deformable portion, and
a first movable portion supported by the first deformable portion, the first movable portion including a first movable electrode facing the first fixed electrode,
a first gap being provided between the first base body and the first deformable portion and between the first base body and the first intermediate portion,
a third gap being provided between the first fixed electrode and the first movable electrode,
the first deformable portion including a first deformed facing surface facing the first base body, and a first deformable surface, the first deformed facing surface being between the first base body and the first deformable surface in a first direction from the first base body to the first movable portion,
the first intermediate portion including a first intermediate facing surface facing the first base body, and a first intermediate surface,
the first intermediate facing surface being between the first base body and the first intermediate surface in the first direction,
with a rise of a temperature, the first deformable surface being deformed into one of a concave shape or a convex shape, the first intermediate surface being deformed into an other of the concave shape or the convex shape, and
the controller being configured to change a first capacitance between the first fixed electrode and the first movable electrode by supplying a current to the first resistance layer.

* * * * *